United States Patent
Ince

(12) United States Patent (10) Patent No.: US 8,064,976 B2
Ince (45) Date of Patent: Nov. 22, 2011

(54) SYSTEMS AND METHODS FOR SIDESSTREAM DARK FIELD IMAGING

(76) Inventor: Can Ince, Leiden (NL)

( * ) Notice: Subject to any disclaimer, the term of this patent is extended or adjusted under 35 U.S.C. 154(b) by 524 days.

(21) Appl. No.: 10/956,610

(22) Filed: Oct. 1, 2004

(65) Prior Publication Data

US 2007/0232874 A1 Oct. 4, 2007

Related U.S. Application Data

(60) Provisional application No. 60/508,347, filed on Oct. 3, 2003, provisional application No. 60/557,792, filed on Mar. 29, 2004.

(51) Int. Cl.
*A61B 5/05* (2006.01)

(52) U.S. Cl. .......................... 600/343; 600/478

(58) Field of Classification Search ............... 600/320, 600/200, 407, 476; 385/115
See application file for complete search history.

(56) References Cited

U.S. PATENT DOCUMENTS

| | | | |
|---|---|---|---|
| 4,948,247 A | 8/1990 | Lapeyre et al. | |
| 4,998,533 A | 3/1991 | Winkelman | |
| 5,178,536 A | 1/1993 | Werly et al. | |
| 5,290,275 A * | 3/1994 | Kittrell et al. | 606/15 |
| 5,377,674 A | 1/1995 | Kuestner | |
| 5,456,252 A | 10/1995 | Vari et al. | |
| 5,561,517 A | 10/1996 | Horiuchi et al. | |
| 5,652,777 A | 7/1997 | Nagai et al. | |
| 5,749,830 A | 5/1998 | Kaneko et al. | |
| 5,912,699 A | 6/1999 | Hayenga et al. | |
| 5,953,477 A * | 9/1999 | Wach et al. | 385/115 |
| 5,964,325 A * | 10/1999 | Davison et al. | 188/330 |
| 5,983,120 A | 11/1999 | Groner et al. | |
| 6,006,001 A | 12/1999 | Alfano et al. | |
| 6,026,314 A | 2/2000 | Amerov et al. | |
| 6,055,451 A * | 4/2000 | Bambot et al. | 600/476 |
| 6,104,939 A | 8/2000 | Groner et al. | |
| 6,134,460 A | 10/2000 | Chance | |
| 6,175,750 B1 | 1/2001 | Cook et al. | |
| 6,219,566 B1 * | 4/2001 | Weersink et al. | 600/317 |
| 6,438,396 B1 | 8/2002 | Cook et al. | |
| 6,449,006 B1 * | 9/2002 | Shipp | 348/70 |

(Continued)

FOREIGN PATENT DOCUMENTS

DE 10119615 10/2002

(Continued)

OTHER PUBLICATIONS

Makisalo et al. Correction of Hemorrhagic Shock-Induced Liver Hypoxia with Whole Blood, Ringer's Solution or with Hetastarch. Res Exp Med 189:397-407. 1989.*

(Continued)

*Primary Examiner* — Parikha Mehta
(74) *Attorney, Agent, or Firm* — Grant Anderson LLP

(57) ABSTRACT

Systems and methods for imaging the reflectance of a substrate, such as a tissue substrate, may include a light source, a light transport body configured to project light from the light source to an examination substrate and transmit light reflected by the examination substrate, and an analysis section in optical communication with the light transport body and having a reflectance avoidance imaging module and at least one of a reflectance spectrophotometry module and a fluorescence imaging module. Methods may include utilizing the microcirculatory flow information, oxygen availability information, and the adequacy of oxygenation of tissue cells information, making an early and sensitive determination regarding states of shock in patients.

9 Claims, 15 Drawing Sheets

U.S. PATENT DOCUMENTS

| | | | |
|---|---|---|---|
| 6,453,183 | B1 | 9/2002 | Walker |
| 6,549,794 | B1 | 4/2003 | Nadeau et al. |
| 6,571,118 | B1 * | 5/2003 | Utzinger et al. ............. 600/476 |
| 6,650,916 | B2 | 9/2003 | Cook et al. |
| 6,690,958 | B1 | 2/2004 | Walker et al. |
| 6,799,075 | B1 * | 9/2004 | Chornenky et al. ........... 607/117 |
| 6,870,620 | B2 | 3/2005 | Faupel et al. |
| 6,975,899 | B2 * | 12/2005 | Faupel et al. ................ 600/476 |
| 7,062,311 | B1 | 6/2006 | Sendai et al. |
| 7,580,133 | B2 | 8/2009 | Ueki et al. |
| 2002/0183601 | A1 | 12/2002 | Tearney et al. |
| 2003/0032936 | A1 | 2/2003 | Lederman |
| 2003/0191398 | A1 | 10/2003 | Motz et al. |
| 2003/0219759 | A1 * | 11/2003 | Rainer et al. ...................... 435/6 |
| 2004/0225222 | A1 | 11/2004 | Zeng et al. |
| 2005/0018202 | A1 | 1/2005 | Wang |
| 2006/0184037 | A1 | 8/2006 | Ince et al. |
| 2006/0241364 | A1 | 10/2006 | Ince |
| 2007/0103683 | A1 | 5/2007 | Wang |
| 2009/0012378 | A1 | 1/2009 | Ince |

FOREIGN PATENT DOCUMENTS

| | | |
|---|---|---|
| WO | WO 95/19134 | 7/1995 |
| WO | WO 96/39927 | 12/1996 |
| WO | WO 97/15229 | 5/1997 |
| WO | WO 99/20646 | 4/1999 |
| WO | WO 99/30608 | 6/1999 |
| WO | WO 00/15101 | 3/2000 |
| WO | WO 00/42912 | 7/2000 |
| WO | WO 00/42912 A1 | 7/2000 |
| WO | WO 00/57157 | 9/2000 |
| WO | WO 01/22741 A2 | 3/2001 |
| WO | WO 02/15788 | 2/2002 |
| WO | WO 02/43561 | 6/2002 |
| WO | WO 02/075242 | 9/2002 |
| WO | WO 02/075289 | 9/2002 |
| WO | WO 03/043492 | 3/2003 |
| WO | WO 2005/032361 | 4/2005 |

OTHER PUBLICATIONS

Nolte et al. Functional Capillary Density: An Indicator of Tissue Perfusion? Int J Microcirc. vol. 15: pp. 244-249. 1995.*

PCT Written Opinion and International Search Report (PCT/IB2004/003845 mailed Jun. 23, 2005).

PCT Written Opinion and International Search Report (PCT/NL2005/000819 mailed Jan. 3, 2006).

Buwaida M, Ince C (2002) *Opening the microcirculation . . . Can casodilators be useful in sepsis*? Intensive care medicine (in press).

Cook, et al., *In vivo vascular study with incident dark-filed illumination*, Trans. Amer. Soc. Artif. Int. Organs, (1973), 348-351, vol. 19.

Coremans, et al., *(Semi-)Quantitative analysis of reduced nicotinamide adenine dinucleotide fluorescence images of blood-perfused rat heart*, Biophysical Journal, (Apr. 1997), 1849-1860, vol. 72.

Groner W, Winkelman JW, Harris AG, Ince C, Bouma GJ, Messmer K and Nadeau R., (1999) *Orthogonal polarization spectral imaging: A new method for study of the microcirculation*. Nature Medicine 5(10): 1209-1212.

Ince C (2000), *Microcirculatory weak units: an alternative explanation*, Crit. Care Medicine 2000 28: 3128-3129. Reply to letter by Schwartz DR, Fink MP 28; 3127-3128.

Ince C (2002) The microcirculation unveiled. Am J of Resp Critical Care eMed (in press). 10. Pennings FA, Bourna GJ and Ince C (2000) *The assessment of determinants of cerebral determinants of cerebral oxygenation and microcirculation. In: The (patho) physiology of the peripheral circulation; The brain update in intensive care and emergency medicine*ed M Pinsky, Publ Springer Berlag. (in press).

Ince C, et al., *Microcirculatory oxygenation and shunting in sepsis and shock*, Crit. Care Med., (1999), 1369-1401, vol. 27, No. 7.

Marthura KR and Ince C (2000). *First clinical use of Orthogonal Polarization Spectroscopy imaging. In: Orthogonal Polarization Spectroscopy*. Prog. Appl. Microcirc 24:94-101.

Mathura KR, et al., *Initial clinical experience with OPS imaging for observation of the human microcirculation. Yearbook of intensive care and emergency medicine*. 2001. Ed J-L Vincent publ. Springer Verlag. ISBN 3-540-41407, pp. 233-245.

Mathura KR, Bouma GJ and Ince C (2001) *Abnormal microcirculation in brain tumors during surgery*. The Lancet 538:1698-1699.

Mathura KR, Vollebrecht KC, Boer K, De Graaf, JC, Ubbink DT, Ince C. *Comparison of OPS imaging and conventional capillary microscopy to study the human microcirculation*. J. Appl. Physiol (2001);91(1):74-78.

Mik B, Donkersloot K, Raat NJH, Iace C (2002) *Excitation pulse deconvolution in phosphorescence lifetime analysis for 02 measurements* in vivo, Photochemistry and Photobiology (in press).

J. Lindert. *OPS imaging of human microcirculation: A short technical report*, Journal of vascular research, (2002):39, 368-372.

Kajiya F, Yada T, Kimura A, Hiramatsu O, Goto M, Ogasawara Y, Tsujioka. *Endocardial coronary microcirculation of the beating heart*, Chapter 16 *Interactive phenomena in the cardiac system*, edited by K. Sideman, S Beyar, R published by Plenum Press (1993).

Sherman, et al., *Incident dark-field illuminations: A new method for microcirculatory study. Angiology*, (May 1971), 295-303, vol. 19.

Siegemund M, Jasper Van Bommel and Ince C. (1999) *Assessment of regional tissue oxygenation*. Intensive care Med. 25:1044-1060.

Slaaf D, Jongsma F, Tangelder G, Reneman R *Characteristics of optical systems for intravital microscopy* Chapter 15 of microcirculatory technology, Edited by Charleton H. Baker and William L. Nastuk, published by Academic press, Inc. (1986).

Spronk PE, Ince C, Gardien MJ, Mathura KR, Oudemans-Van Straaten HM, Zandstra DF (2002) *Nitroglycerin promotes microvascular recruitmentin septic shock after pressure guided resuscitation*. The Lancet (in press)7.

Toyotaka Yada, Osamu Hiramatsu, Akihiro Kimura, Masami Goto, Yasuo Ogasawara. In vivo *observation of subendocardial microvessels of the beating porcine heart using a needle-probe videomicroscope with a CCD camera*. Circulation research, vol. 72, No. 5, (May 1993).

Tugtekin IF, Radermacher P, Theisen M, Matejovic M, Stehr A, Ploner F, Mathura K, Ince C, Georgiedd M and Trager K. (2001) *Increased ileal-mucosal-arterial PC02 gap is associated with impaired villus microcirculation in endotoxic pigs*. Intensive care med 27 (4):757-766.

Tugtekin I, et al., *Endotoxin-induced ileal mucosal acidosis is associated with impaired villus microcirculation in pigs*, Prog. Appl. Microcirc. Basel, Kager, (2000), 61-69, vol. 24.

Van Bommel J, Siegemund M and Ince C. (2001) *Redistribution of microvascular oxygen pressure in the pig intestines in hemodilution and sepsis. In: Mechanisms of organ dysfunction in critical illness*. Ed MP Fink, T Evans, JL Vincent publ Springer Verlag. (in press).

Van Der Laan L, Coremans A, Ince C, Bruining HA (1998) *NADH videofluorimetry to monitor the energy state of skeletal muscle* in vivo. J Surg Res 74:155-160.

Vollebregt KC, Boer K, Mathura KR, De Graaff JC, Ubbink DT and Ince C (2001) *Impaired vascular function in women with pre-eclmpsia observed with OPS imaging*. Br J Obst Gyn 41: 1148-1153.

Lijckle van der Iaan et al., NADH Videofluorimetry to Monitor the Energy State of Skeletal Muscle in Vivo, Journal of Surgical Research, 74 (2), p. 155-160 Feb. 1988.

U.S. Appl. No. 11/397,178, filed Apr. 3, 2006, Can Ince.

Office Action, Mail Room Date: Jan. 10, 2008 from U.S. Appl. No. 11/397,178, filed Apr. 3, 2006.

Office Action, Mail Room Date: Oct. 3, 2008 from U.S. Appl. No. 11/288,844, filed Nov. 28, 2005.

Office Action, Mail Room Date: Oct. 19, 2007 from U.S. Appl. No. 11/288,844, filed Nov. 28, 2005.

Office Action, Mail Room Date: Jan. 5, 2011 from U.S. Appl. No. 11/720/469 on Jun. 20, 2009.

Office Action, Mail Room Date: Aug. 2, 2010 from U.S. Appl. No. 11/288,844, filed Nov. 28, 2005.

* cited by examiner

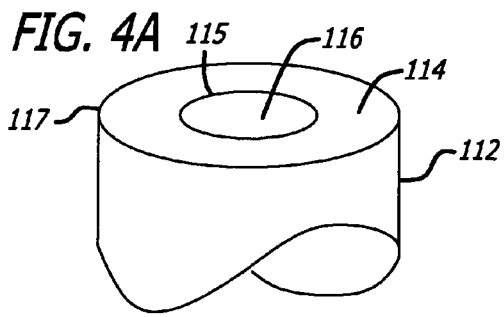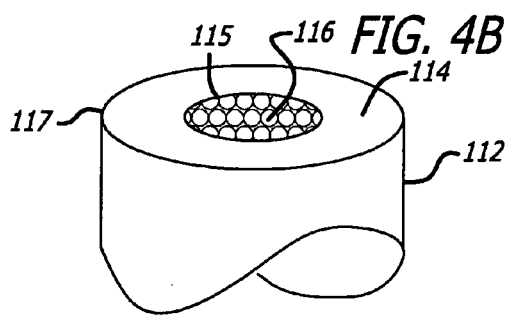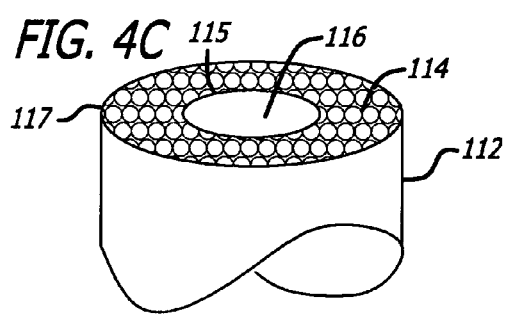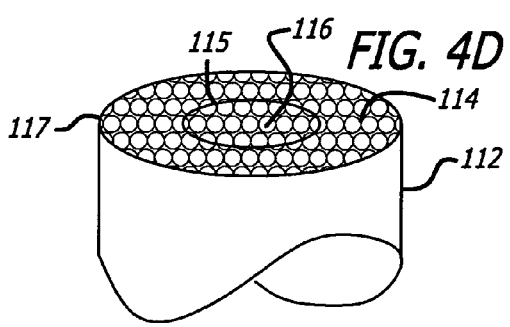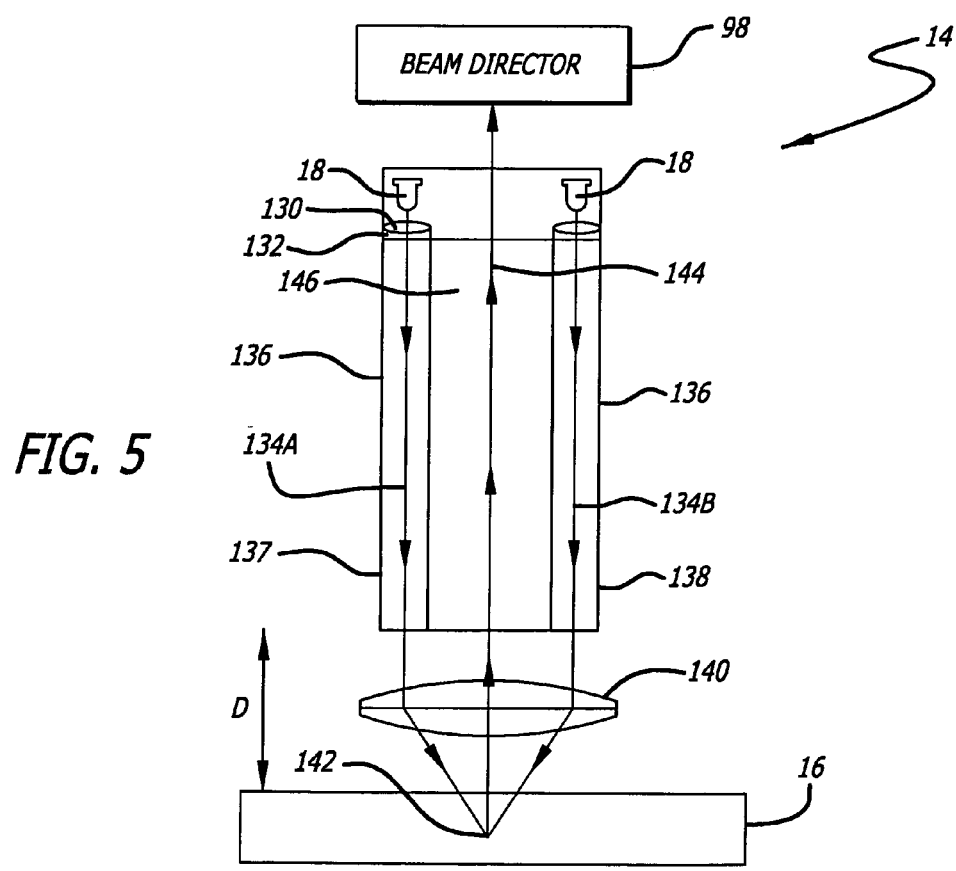

SYSTEMS AND METHODS FOR SIDESSTREAM DARK FIELD IMAGING

CROSS REFERENCE TO RELATED APPLICATIONS

The present application claims priority to and incorporates by reference in its entirety the contents of U.S. Provisional Patent Application Ser. No. 60/508,347, filed on Oct. 3, 2003, and naming Can Ince as inventor. The present application also claims priority to and incorporates by reference in its entirety the contents of U.S. Provisional Patent Application Ser. No. 60/557,792, filed on Mar. 29, 2004, and naming Can Ince as inventor.

BACKGROUND

Currently, physicians typically monitor a number of systemic (e.g. the macrocirculation) hemodynamic parameters when diagnosing and monitoring of the hemodynamic condition of patients. For example, blood flow and pressure are regularly monitored. In addition, a blood sample may be withdrawn from the patient to determine the oxygenation of the red blood cells as well as the oxygen carrying capacity of the circulating blood. Furthermore, a biopsy may be required to determine the functional state of tissue cells (e.g. the oxygenation and viability of tissue cells) of the organ system.

While monitoring these macrohemodynamic parameters has proven successful in diagnosing and monitoring a number of conditions, several shortcomings have been identified. For example, examining macrocirculatory parameters provides little or no information relative to the microcirculatory (i.e. hemodynamics and structure of blood vessels smaller than 250 microns) characteristics of patients. Current research has shown that distress at the microcirculatory level involved in a large number of disease states is not discoverable by monitoring macrocirculation. As such, diseases or other complications evident through microcirculatory monitoring may go undetected and untreated.

It is believed, for example, that improved clinical observation of the microcirculation of human organs would be extremely useful in assessing states of shock such as septic, hypovolemic, cardiogenic and obstructive shock in patients and in guiding resuscitation therapies aimed at correcting this condition. In particular, it has been found that the active recruitment of the microcirculation maybe an important component of resuscitation. Additionally, improved clinical observation of the microcirculation would be helpful in observing gross circulatory abnormalities in pathologies such as tumors and cardiovascular disease.

To fully monitor the function of the microcirculation, that is the structure and profusion of vessels smaller than 250 micrometers, in addition to measuring blood flow it is important to measure and assess whether the blood cells are successful in transporting their oxygen to the microcirculation and thereafter to the surrounding tissue cells. Of particular importance is the assessment of the profusion of the capillaries, which are between approximately 5 to 10 micrometers, because it is at this level that oxygen is transported by the red blood cells to the tissue cells of the organ for the purposes of respiration and survival. Monitoring the functional state of the microcirculation can thus be regarded as monitoring the ultimate efficacy and function of the cardiovascular system to deliver adequate amounts of oxygen to the organ cells.

It is believed, for example, that improved and comprehensive imaging of the properties of the microcirculation would be helpful in observing and assessing the beneficial effects of therapy during the resuscitation of shock patients. An accurate assessment of both blood flow and oxygen availability at the level of the microcirculation could thus provide a clinical tool with which to guide resuscitation. A comprehensive way to monitor the microcirculation could generally provide an improved clinical diagnostic tool for evaluating and monitoring the functional state of the microcirculation in the perioperative phase of treatment.

To date, there have been limits to a comprehensive monitoring of the microcirculation in order to provide the benefits discussed above. Specifically, several factors have limited the ability to evaluate the oxygen transport variables of the microcirculation comprehensively. For example, devices which contact the surface of the microcirculation inhibit their ability to obtain quantitative information about blood flow in the various categories of micro-vessels in the microcirculation by impeding flow due to exerted pressure. Furthermore, current devices and techniques for imaging the microcirculation do not provide the additional needed information about the oxygen availability in the microcirculation or about the adequacy of oxygenation of the tissue cells. This information would be very helpful in assessing the functional state of the microcirculation, specifically its function in allowing adequate transport of oxygen to the tissue cells. Thus, there is a need for an improved system and method for a more effective and a more comprehensive clinical observation of the microcirculation which includes these parameters.

SUMMARY

The system and method disclosed herein provides comprehensive information about the microcirculation by providing multiple modes of optical spectroscopy and imaging in a manner which does not influence the microcirculation. In one aspect, the system avoids reflection of light from the tissue in the various imaging modes. This reflectance avoidance can be provided by reflectance filtering, such as orthogonal polarization or cross-polarization of light or dark field imaging, or by sidestream dark field imaging, wherein, for example, incident and reflected light may not travel down the same pathway.

In order to image flowing cells in the microcirculation, light has to be illuminated on to the surface of the organs, which is the substrate, and a magnifying lens may be used. Use of a specific wavelength of light (e.g. green light) may allow for better observation of the contrasting red blood cells due to the absorption characteristics of the hemoglobin (hereinafter Hb) in the red blood cells. However, surface reflections from the substrate can interfere with the ability to clearly visualize the underlying microcirculation structures and the flowing blood cells therein. Filtering out of these surface reflection by various methods allows visualization of the blood flow in the underlying microcirculation on organ surfaces by measurement of the images of the moving cells. Reflectance filtering can be achieved by a number of techniques which are known to those of skill in the art. The system and method disclosed herein may utilize some of these known techniques, but some novel ones are disclosed as well.

In some embodiments, the system and method utilizes reflectance avoidance by known techniques of reflectance filtering, such as: 1) OPS imaging, whereby illuminating light and reflected light travel down the same light guide; or 2) Mainstream Dark Field imaging, whereby illuminating light and reflected travel down the same light guide but peripheral illumination is achieved by directing the light through, for example, a hole in a 45° mirror or design of a lens in the illuminating pathway, which impedes transmission of the light through the middle, and/or a lens which poorly allows transmission of the light through the centre is put in the pathway of the light to achieve the same effect.

In other embodiments, a novel method of reflectance avoidance is disclosed which is an alternative to reflectance filtering. This novel approach, referred to herein as Sidestream Dark Field imaging (hereinafter SDF), utilizes external direct light on the tip of the light guide to achieve reflectance avoidance whereby incident and reflected light do not travel down the same pathway. This form of imaging can be provided in combination with a hand-held microscope. A feature of SDF imaging is that illuminated light and reflected light travel via independent pathways. With this modality, the illumination can be placed directly on the tissue and the observations can be made adjacent to it without light crossing over between two paths. The illuminating light source is typically placed on or near contact with the tissue. The scattering of the reflected light is thus outside of the image as most light cross over is below the tissue surface. To date, Mainstream Dark Field imaging has been described as a way of improving contrast and lowering surface reflectance, but it typically utilizes illumination and reflectance light paths that travel up and back the same pathway. In the past, SDF illumination has been applied by ring illumination to improve epi-illumination. It is believed, however, that it has not been applied to achieve true dark field illumination by illuminating one segment of a substrate and observing in another segment images of the microcirculation and its flowing cells. It is believed that SDF imaging has characteristics which make it superior to other modes of imaging.

The foregoing reflectance avoidance imaging systems, whether they utilize OPS, Mainstream Dark Field illumination, or SDF illumination, can be used to enable the comprehensive evaluation of the functional state of the microcirculation. This is achieved by an analysis of the moving cells in the images, which permits the quantitative measurement of red blood cell flow in the capillaries, as well as in the larger vessels of the microcirculation. This measurement is believed to represent a truly sensitive measurement which is indicative of cardiovascular disease and dysfunction. Laser Doppler measurements, for example, provide an over all flux of moving particles in an unidentified compartment of the circulation, but do not have the specificity for measurement of cellular profusion of these smallest capillaries.

The system and method disclosed herein, in providing reflectance avoidance in combination with optical magnification, provides a superior method of measurement of the functional state (e.g. profusion/oxygenation) of the microcirculation. Next to the measurement of profusion, morphological characteristics of the microcirculation, such as functional capillary density and micro-vessel morphology, can be measured using reflectance avoidance imaging. Homogeneous profusion of the capillaries is a prerequisite for normal function of the microcirculation and abnormal profusion or diminished capillary profusion is considered an early and sensitive indicator of cardiovascular disease and failure.

The present application thus relates to a variety of imaging systems for analyzing the reflectance of an examination substrate. While the imaging system disclosed herein may be used to analyze the reflectance characteristics of a variety of substrates, it is particularly well suited for non-invasively imaging the micro-circulation with a tissue sample.

In one embodiment, the present application discloses a system for imaging the reflectance of a substrate and includes a light source, a light transport body configured to project light from the light source to an examination substrate and transmit light reflected and scattered by the examination substrate, an analysis section in optical communication with the light transport body and having an orthogonal polarization spectral imaging module or any other of the reflectance avoidance imaging systems, and at least one of a reflectance spectrophotometry module and a fluorescence imaging module.

In an alternate embodiment, the present application discloses an orthogonal polarization imaging system and includes a light source configured to emit white light, a first polarizer to polarize the white light, a light transport body to transport the polarized light to an examination substrate and reflect light from an examination substrate, a second polarizer to filter the light reflected and scattered by the examination substrate, a filter bank containing at least one wavelength filter to filter the reflected light, and an image capture device in optical communication with the light transport body and configured to image the reflected light.

In still yet another embodiment, the present application discloses a method of imaging the reflectance of a substrate and includes illuminating an examination substrate with light, transmitting a portion of light reflected by the examination substrate to a reflectance spectrophotometer, determining a concentration of hemoglobin within the examination substrate based on a spectral characteristic of the examination substrate with the reflectance spectrophotometer, transmitting a portion of the light reflected by the examination substrate to an orthogonal polarization spectral imaging module, and measuring a flow through a vessel within the examination substrate with an orthogonal polarization spectral imaging module.

In one embodiment, the present application discloses a novel manner of applying dark field imaging on the tip of a light guide to provide clear images of the microcirculation on human organ surfaces. This can be accomplished by putting light emitting diodes (LED's) around the tip of the light guide in combination with a separator so that the illuminating light does not enter the reflection light guide directly by surface reflection, but via the internal structures inside the substrate. This modality of reflectance avoidance is a form of dark field imaging which we have called Sidestream Dark Field or SDF imaging and provides remarkably clear images of the microcirculation.

In some embodiments, reflectance avoidance imaging is used to obtain a microcirculatory perfusion index as well as a heterogeneity of flow index in a device that does not impact flow patterns. This may be accomplished by using non-contact modes such as, for example, using a long focal length, immobilizing the device and substrate by suction at the tip, or utilizing a spacer between the tissue and the light emitting tip.

In one such embodiment, a novel, "castle" type of spacer is utilized to provide distance from the examining substrate and to avoid pressure of the tip on the substrate. In another embodiment, a needle camera is utilized with a spacer to provide a dark field illumination device. In yet another embodiment, a suction device is used with reflectance avoidance imaging techniques.

In another embodiment, a distance spacer is used to achieve reliable capillary perfusion measurements whereby the tip of the image guide does not impede flow in the microcirculation by pressure. In yet another embodiment, reflectance avoidance imaging is used in combination with a space through which fluid, drugs or gasses can be perfused.

In one embodiment, a disposable tip attaches to the end of the device and is removed by a release mechanism so that it can be disposed of without having to touch the disposable.

The utilization of reflectance avoidance in the present invention provides an improved method of observing microcirculatory hemodynamics and functional morphology.

Image analysis can provide a plurality of clinical parameters which will have utility for various clinical conditions. The method and device will assist in providing a perfusion index such as a measure of functional capillary density, which is the number of perfused micro-vessels showing per field observed. Other parameters include the distribution and heterogeneity of micro-vascular flow, torsion and functional morphology of the blood vessels, the distribution of diameters of blood vessels, white blood cell kinetics, abnormal red blood cell kinetics (e.g. the presence of micro-vascular coagulation, sludging or adhesion).

For a comprehensive assessment of the functional state of the microcirculation, it may be preferable to have more than just perfusion information. It would also be useful to have Information about the amount of oxygen bound to the Hb, which can be provided by reflectance spectrophotometry, and information as to whether the tissue cells are getting sufficient amount of oxygen, which can be provided by measuring tissue $CO_2$ by sensing the $CO_2$ in the inside of the disposable, using, for example, $CO_2$ sensitive fluorescence quenching dyes. The light guide can then be used to excite the dye with a pulse of light and a detector which measures the $CO_2$ dependent quenching of fluorescence life time would provide the measurement. Also, mitochondrial energy states by NADH via fluorescence imaging can be obtained. Information may be obtained about whether there is movement of the red blood cells in the microcirculation, whether the red blood cells are transporting oxygen (i.e. Hb saturation), and whether the tissue cells are getting enough oxygen (tissue $CO_2$ measurement and/or NADH fluorescence imaging).

In some embodiments, reflectance spectrophotometry in conjunction with reflectance avoidance is used to assess the adequacy of oxygen availability. This may provide for the assessment of microcirculatory oxygen transport. In some embodiments this can be accomplished by an analysis of the full reflected spectrum of light (e.g. 400-700 nm). In other embodiments it is accomplished by an analysis of discrete wavelengths outputs of a color sensitive imaging device. Microcirculatory Hb saturation, microcirculatory Hb concentration, and microcirculatory hematocrit can all be measured.

In some embodiments, the SDF imaging technique is combined with the use of different wavelengths LED's wherein the images are normalized and Beer Lambert equations are applied.

In some embodiments, NADH fluorescence imaging is used to measure the adequacy of the need for mitochondrial oxygen. This can be used to assess tissue cell dysoxia.

In some embodiments, fluorescence spectroscopy is used for tissue cell diagnostics using endogenous molecules, reporter genes or external indicator dyes. With appropriate filters, apoptosis can be detected (e.g. via annexin fluorescence), green fluorescent labeled cells used in gene therapy could be located in terms of their efficacy in homing in on the target.

In one embodiment, a method of imaging the microcirculation by avoiding surface reflections is combined with reflectance spectrophotometry, Raman spectroscopy, fluorescence spectroscopy and/or other types of spectroscopic modalities, such as light scatter measurements or optical coherence tomography.

In some embodiments, the device is a light guide based system wherein emission and excitation light travels via light guides. In some embodiments, the images are detected at the tip with a tip camera. The device may have a fused silicon lens which will allow 360 nm to pass in order to enable NADH fluorescence imaging. The device can be either hand held or a flexible endoscopic type.

In addition, to direct contact imaging, the reflectance avoidance imaging system disclosed herein may also be capable of operating in a non-contact mode which makes use of a spacer to avoid pressure in the tissue surface which may impede blood flow therethrough. Various spacer options exist, including:

a. plastic upside down cup attached as disposable;

b. a doughnut shaped spacer (which can be inflatable) with an upside down situation/cup;

c. a device (e.g. a plug for around the scope end), such as a concentric ring with suction ports, for providing suction through little holes around the perimeter of the scope thereby immobilizing the perimeter but leaving the microcirculation in the field of view unstressed; or d. a transparent cushion either solid, air inflatable or filled with fluid.

What is also disclosed is a non-contacting tip for endoscopic use. In one embodiment, long focus distance imaging can be used to observe retinal microcirculation. This modality can be used to monitor eye diseases and as a monitoring tool during surgery to monitor brain function non-invasively. In the retinal application imaging light can be pulsed and small clips of moving images used for monitoring, thus minimizing retinal light exposure.

In one embodiment, the system is configured to operate in a no contact mode without use of a spacer. Thus, the system may be used during brain surgery or heart surgery. Any movement of the object surface can be corrected by image processing either on-line or after a delay.

In one embodiment the light guide system has an L-shape at the end. Here a 45° mirror creates the bend and LED illumination, using SDF, imaging is present at the tip, with or without a spacer and/or suction module. This embodiment may be used to inspect the sides of hollow spaces such as is present in the digestive track.

In another embodiment, large objective magnification may be used. For example, image processing software may be used to immobilize or stabilize the images, thereby allowing for better image processing of the movements.

In still another embodiment, magnification of the substrate image can be influenced in several ways. For example, different lenses may be used (different spacer on the tip), or movement of exiting lenses by an opto-mechanical system, or in the electronic mode a larger number of pixel CCD or CMOS chips, which are known to those of skill in the art, or a larger density of pixels in the chip can be utilized. Movement of the CCD or CMOS can also be used to influence magnification.

In still another embodiment, any number of specified color cameras may be used with the present system. For example, a choice of color or combination of colors would allow images to be generated of the saturation of the Hb of the red blood cells in the microcirculation. A further embodiment involves looking at only the red output of a color camera and to filter out of the rest of the image. This would result in red cells moving in a white background.

Use of a high speed rate (i.e. higher than video rate) can be used for obtaining a proper velocity measurement in conditions in which red blood cells are moving faster than the video rate.

In some embodiments, a $CO_2$ measurement of the tissue in the field of view can be made simultaneously with a reflectance avoidance flow measurement and an oxygen availability measurement, such as with spectrophotometry, as a measure of tissue wellness.

In one embodiment, a disposable spacer (e.g. upside down cup) may be employed. In this embodiment, a $CO_2$ sensing dye can be impregnated with which $CO_2$ can be sensed within the cup environment. The dye works to provide a fluorescence decay measurement and the excitation and emission light of this dye in the disposable tip can be measured through the light guide. The $CO_2$ measurement can be combined with a reflectance avoidance flow measurement, such as an OPS or SDF imaging based perfusion measurement. Furthermore, a $CO_2$ probe may be inserted into the nose of a patient to assess tissue pCO2 and combine this information with simultaneously measured perfusion (e.g. by OPS or SDF imaging) and oxygen availability (spectrophotometry) measured sublingually. In another embodiment, the $CO_2$ probe may be used rectally. These measurements may be made continuously. The sensor may be embedded within a pliable of cushioning material. For example, the sensor may be positioned within a sponge so as to trap and sense the $CO_2$ sufficiently.

The $CO_2$ sensor can be used in the nose and/or rectally as alternative locations for a separate sensor which is then integrated in the measurement. This can be in single or in multi mode. The latter technique, which makes use of more than one $CO_2$ sensor, will give information about regional heterogeneity. Using multi locations is believed to be a new use of a $CO_2$ measurement.

In some embodiments, a laser can be included as a therapeutic modality. This can be accomplished, for example, by the use of dark field illumination in which the laser goes through the hole in the slanted mirror. In this embodiment, reflectance avoidance imaging is combined with the use of the laser for photodynamic therapy (e.g. for cancer) or to coagulate micro-vessels in port wine stains or other cosmetic corrective procedures.

In another embodiment, reflectance avoidance imaging is used to observe the microstructure of the wound, and temperature is sensed by a solid state or thermo-sensitive color sensor as well as by optical spectroscopy to measure the water content. It is thereby that wound perfusion (via e.g. OPS or SDF imaging), wound temperature and edema (water content) will give a comprehensive measurement of the phase of wound healing and allow assessment of the response to therapy.

In the photodynamic embodiment (where the patient receives a photosensitive drug) it is possible to apply fluorescence in combination with reflectance avoidance for detection of the drug (which accumulates in tumors) or for enhanced fluorescence in ALA induced protoporphyring fluorescence. Combining a therapeutic laser in the device would make it possible to deliver photodynamic therapy directly to the area of high fluorescence.

Alternative illumination modalities may include pulsing the LED illumination in combination with synchronization with a camera for the measurement of high blood flow velocities. Another alternative includes the use of an optical foil, acting as a light guide, or other material which may be wrapped around the tip of the probe providing illumination from the side of the tip as an alternative way of illuminating the object and accomplishing reflectance avoidance. This is similar to the method which is accomplished by the use of optical fibers placed around the out side of the scope.

Other embodiments which include laser therapies include the use of reflectance avoidance imaging to verify the effectiveness and allow for the accurate titration of laser doses. A second example is the use of photodynamic therapy for on-line treatment of photosensitized tumors.

In another embodiment, a custom spacer is disclosed in which it is possible to introduce a drug or gas to the field of observation and measure the reactivity of the blood vessels (i.e. losses of which are an indication of poor function). This spacer could be a suction spacer which would provide space in the field of view to ensure that there is no contact with the tip and also provide space to inject a drug (for microcirculatory responsiveness) or for calibration that may be needed for the embodiment which utilizes a $CO_2$ sensor placed in the probe. Drugs which can be considered challenges to the microcirculation are vasodilators acting on specific locations of the microcirculation e.g. acetyl choline, lidocaine or nitrate. Others include vasopressors, such as noradrenaline or dobutamine. This modality can also be used in local treatment of tumors by application of a topical administration of a chemotherapeutic drug.

Measuring the reactivity of the blood circulation to challenges (also given systemically) via, for example, trend measurements, yield parameters which give additional information than a snap shot analysis. Response to therapy of the microcirculation can be monitored continuously providing on-line information about the functional state of the microcirculation during illness.

A further challenge can be induced through a specialized spacer which applies a momentary suction pulse and measures the time of microcirculatory refill.

In some embodiments multi-wavelength imaging can be used for the measurement and analysis of Hb saturation images. The object is sequentially or simultaneously illuminated by specific colored LED's, placed in SDF mode, which are chosen at specific wavelengths along the absorption spectrum of Hb, such that when combined in a composite image they provide an image of the distribution of Hb saturation (or Hb concentration or Hematocrit) of the cells of the microcirculation. A second embodiment for achieving the same objective utilizes white light. The reflected light is then split by a multi-wavelength optical member which may consist of mirrors and filters which project two or more images each at a different wavelength onto the imaging device to allow reconstituted saturation images to be made.

In one embodiment the use of fluorescence SDF imaging (endogenous leucocyte fluorescence), or observing light scatter, to view differences between cells moving in the circulation (i.e. leucocytes scatter more light than red blood cells) and combining such imaging, with or without filtering of special wavelengths, optical conditions permit the observation and quantification of the amount of leucocytes flowing in the microcirculation. Such a measurement would allow quantification of the immune status of the observed field of view by counting the amount of leucocytes and or observing the kinetics of cell sticking or rolling.

In one embodiment, annexin fluorescence can be used for the detection of apoptotic cells. A combination of fluorescence techniques includes but is not limited to annexin-labeled cells which will allow for the visualization of apoptotic cells which are directed to programmed cell death, a precursor to necrosis and cell death. These measurements may be important in assessing cell failure in cardiovascular disease, sepsis and in identification and staging of the severity of cancer, or other stages of diseases such as inflammatory bowel disease. In this application fluorescence labeled annexin is administered to the patient, or applied topically to the site of interest and utilizes the fluorescence mode of the scope. In the fluorescence mode of the scope we describe a hand tool (a fluorescence boroscope) such as described for the reflectance avoidance imaging but in which fluorescence modality is utilized. Reflectance avoidance imaging can be used to improve fluorescence imaging, by filtering or avoiding surface reflections, and can be applied in the boroscope application or also in fluorescence endoscopy where, to date, the combination of fluorescence and reflectance avoidance imaging has not been disclosed.

In this embodiment, the appropriate choice of filters can be used to image mitochondrial energy states (NADH levels) through the use of fluorescence. NADH in vivo fluorescence imaging involves dual wavelength fluorescence combined with reflectance avoidance imaging to correct for changes in absorption in the image, which can be caused by variation in Hb (which is an absorber) in the vessels in the image (results in heterogeneous images). In addition, fluorescence spectrophotometry may be combined with reflectance avoidance imaging to allow cell diagnostics during surgery directly at the bedside. Tissue cell diagnostics will target the functional state of the mitochondria by measurement of the energy of the mitochondria by NADH fluorescence, the gold standard for assessment of tissue dysoxia. Such fluorescence imaging can also be used in conjunction with diagnostic dyes for identification of apoptosis or tumor cells and reporter genes during gene therapy. Combination of fluorescence dyes and cell labeling techniques can be used by this modality (with appropriate filters) to observe and quantify the degree of degradation of the glycocalix lining of the endothelia cells. This observation provides a microcirculatory indication of the severity of cardiovascular disease. Finally measurement of the time course of transport through the microcirculation of a pulse of fluorescent dye allows microcirculatory flow at the capillary level to be quantified when detected by fluorescence.

In some embodiments, reflectance avoidance imaging will be combined with Raman spectroscopy, thereby combining microcirculatory reflectance avoidance imaging with information about the constituents of the tissues.

The above embodiments can be used in an endoscopy mode. For example, dark field endoscopy, OPS imaging, and\or side illumination can be used to make observations in the gastric tract, with for example, the L-tip device discussed above. Polarization can be achieved at the tip of a flexible endoscope. Dark field illumination can be used in the same way by concentric illumination. A light conducting foil can be used at the outside. A 45° mirror can be included at the tip for observation of the sides of the gastric tubes. Thin scopes can be made for pediatrics.

In some embodiments, optical coherence tomography can be used for measurement of optical path-length using Beer Lambert as a quantitative measurement.

Sublingual Near Infra-red Spectroscopy can be used in the transmission mode or in the reflectance mode to measure total oxygenation of the tongue.

The foregoing methodologies for comprehensive imaging of the microcirculation provide a useful clinical tool in assessing states of shock such as septic, hypovolemic, cardiogenic, and obstructive shock in patients and in guiding resuscitation therapies.

Other objects, features, and advantages of the imaging system and method disclosed herein will become apparent from a consideration of the following detailed description.

BRIEF DESCRIPTION OF THE DRAWINGS

The imaging system of the present application will be explained in more detail by way of the accompanying drawings, wherein:

FIG. 4A shows a perspective view of an embodiment of a light transport body of a light transport section;

FIG. 4B shows a perspective view of an alternate embodiment of a light transport body of a light transport section;

FIG. 4C shows a perspective view of another embodiment of a light transport body of a light transport section;

FIG. 4D shows a perspective view of still another embodiment of a light transport body of a light transport section;

FIG. 5 shows a schematic diagram of another embodiment of a light transport section configured to project light on and receive reflected light from an examination substrate;

DETAILED DESCRIPTION

Figure 1:
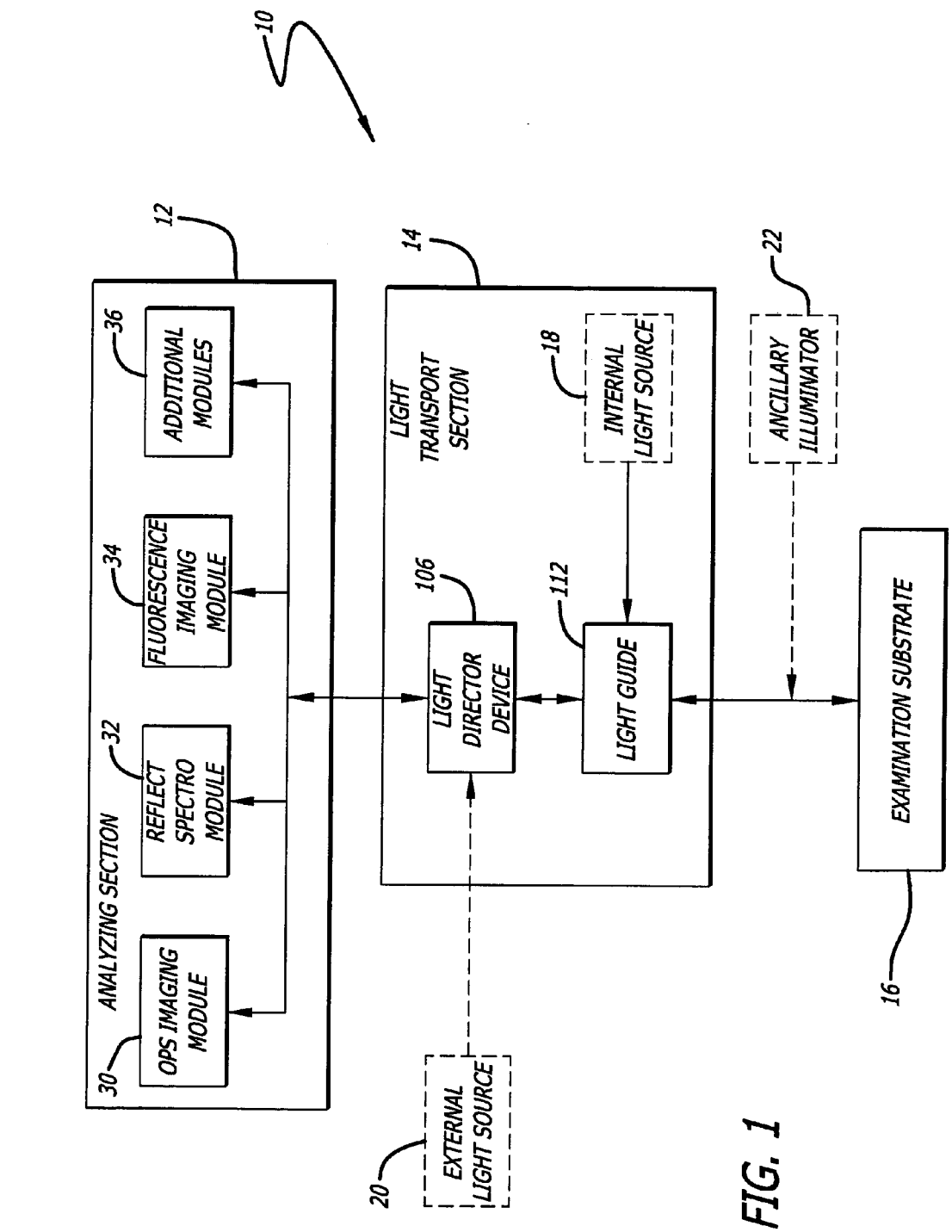
FIG. 1 shows a block diagram of an embodiment of an imaging system for analyzing light reflected from an examination substrate.

FIG. 1 shows a block diagram of an embodiment of a reflectance imaging system. The imaging system 10 includes an analyzing section 12 and a light transport section 14 configured to project light on and/or receive reflected light from an examination substrate 16. In one embodiment the light transport section 14 may include an internal light source 18 therein configured to provide light of at least one selected wavelength and/or polarization to the examination substrate 16. Optionally, the internal light source 18 may be used with or may comprise a source of white or full spectral light thereby enabling spectral analysis of light reflected by the examination substrate 16. In an alternate embodiment, an external light source 20 may be in optical communication with the light transport section 14 and configured to illuminate the examination substrate 16. Optionally, the imaging system 10 may include both an internal light source 18 and an external light source 20. As such, the internal and external light sources may have the same or different wavelengths and/or polarizations. In another embodiment, an ancillary illuminator 22 may be used to illuminate the examination substrate 16. As shown, the ancillary illuminator 22 directly illuminates the examination substrate thereby foregoing the light transport section 14. The various components of the analyzing section 12 and the light transport section 14 will be described in greater detail below.

Referring again to FIG. 1, in one embodiment the analyzing section 12 includes any number of modules configured to analyze light reflected from the examination substrate 16 and transported to the analyzing section 12 by the light transport section 14. In the illustrated embodiment, the analyzing section 12 includes an orthogonal polarization spectral (OPS) imaging module 30, a reflectance spectrophotometry (RFS) module 32, and a fluorescence (FLS) imaging module 34. Any number of additional modules 36 may be included in the analyzing section 12. Exemplary additional modules include, without limitation, Raman spectroscopy modules, optical coherence tomography modules, dark field imaging including side stream dark field imaging (See below), and various light scattering measurement modules.

Figure 2:
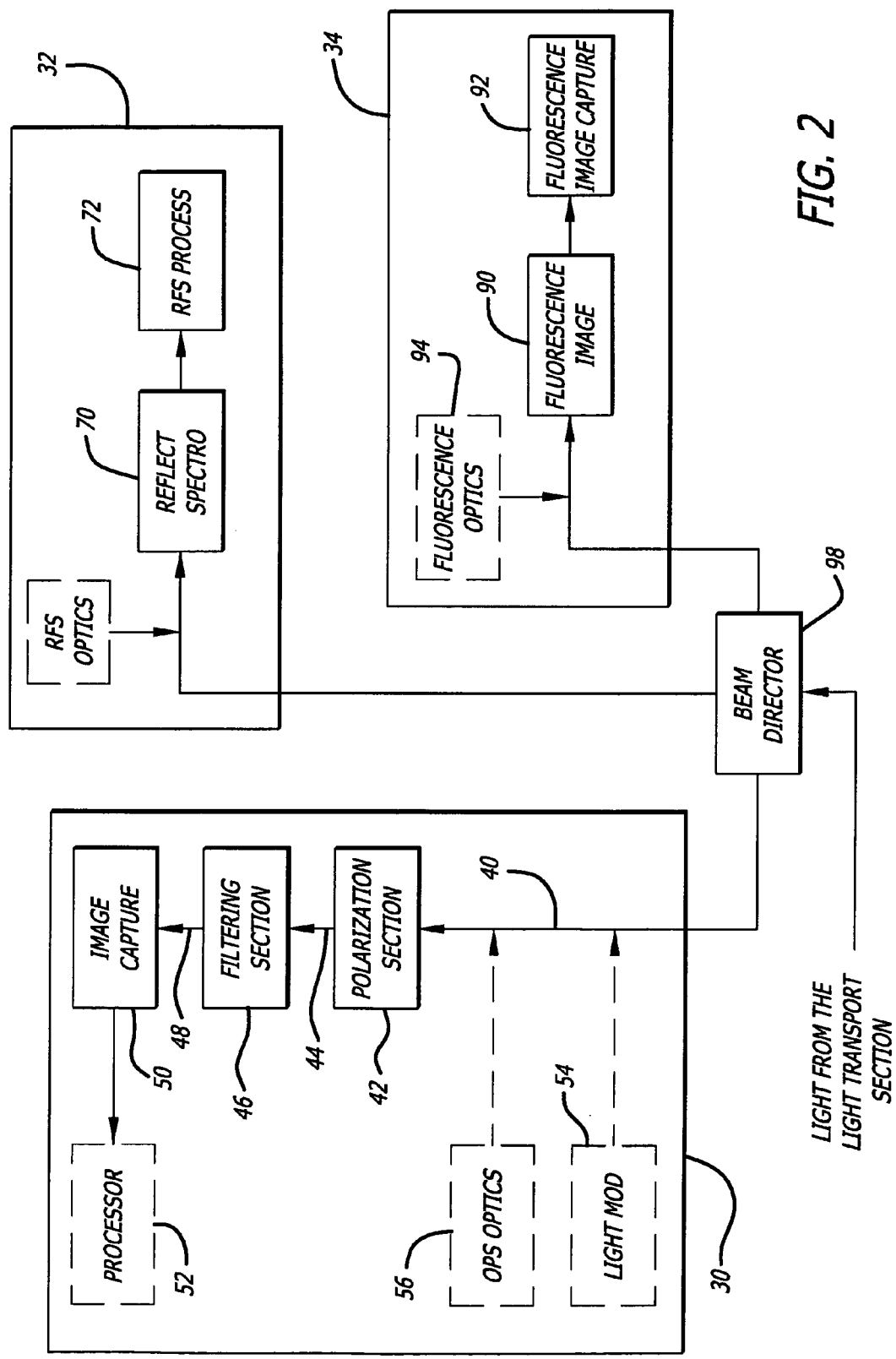
FIG. 2 shows a block diagram of an embodiment of an analyzing section of an imaging system.

As shown in FIGS. 1 and 2, the OPS imaging module 30 receives a light sample 40 from a beam director 98. The light sample comprises light reflected from the examination substrate 16 and transmitted to the beam director 98 by the light transport section 14. As such, the OPS imaging module 30 is configured to image the examination substrate 16 using wither dark field or non-dark filed illumination. Thereafter, the light sample 40 may encounter a polarizing section 42 having one or more optical polarizers therein. The polarizing section 42 permits only light of a selected or desired polarization to transmit therethrough, thereby filtering the light reflected by the examination substrate 16 and improving image quality. IN an alternate embodiment, the OPS imaging module 30 may incorporate a variety of other optical devices or methodologies to optimize image quality. The polarized light 44 is then incident upon a filtering section 46 having one or more optical filters therein. For example, in one embodiment the filtering section 46 contains at least one narrow band pass filter therein configured to permit light within a desired wavelength range to be transmitted therethrough. Exemplary narrow band pass filters include, without limitation, from about 380 nm to about 450 nm (violet filter), from about 445 nm to about 510 nm (blue filter), from about 495 nm to about 580 nm (green filter), from about 575 nm to about 595 nm (yellow filter), from about 590 nm to about 625 nm (orange filter), from about 615 nm to about 710 nm (red filter), and from about 690 nm to about 910 nm (color or photo infrared filter). Optionally, the OPS imaging section 30 may include filters enabling ultraviolet radiation to transmit therethrough. In an alternate embodiment, the filtering section 46 receives light from the light transport section 14 prior to the light sample 40 being polarized.

Referring again to FIG. 2, the filtered light 48 is then transmitted from the filtering section 46 to an image capture device 50. Exemplary image capture devices 46 include, without limitations, charge coupled devices (CCD) and photomultiplier devices. For example, in one embodiment a CCD chip having about 1000 by 1000 pixel resolution or higher may be used. Optionally, images captured at various wavelengths may be captured and compared to permit image normalization. In an alternate embodiment, an image capture device 50 may be utilized to correct for motion effects and aberrations. The image capture device 50 forms an image of light reflected from the examination substrate 16 and transmitted to the OPS imaging section 30 by the light transport section 14. (See FIG. 1). In the illustrated embodiment, the image capture device 46 is in communication with a processor and display device 52. The processor and display device 52 may be used to process information from the image capture device 50 and display the information in any number of ways. Exemplary processor and display devices include, without limitations, computers and display terminals.

As shown in FIG. 2, the OPS section 30 may include a light modulator 54 and/or an OPS optics suite 56. The light modulator 54 may be used to segment the sample light 40, thereby providing a stroboscopic effect thereto. Exemplary light modulators 54 include, without limitations, light choppers, shutters, and light valves including liquid crystal light valves. An OPS optics suite 56 may be used to focus, defocus, collimate, or otherwise refine the light sample 40 transmitting through the OPS imaging section 30. Exemplary components which may be used within the OPS optics suite 56 include, without limitations, mirrors, positive lenses, negative lenses, acromats, compound lenses, astigmats, windows, flats, adaptive optics, holographical optical elements, spatial filters, pinholes, collimators, stages, and beam splitters. The light modulator 54 and the OPS optics suite 56 may be positioned at various locations within the OPS imaging section 30.

Referring again to FIG. 2, the reflectance spectrophotometry module 32 includes a spectrophotometer 70 coupled to a RFS image processor 72 for computing and displaying spectral characteristics of the light reflected from the examination substrate 16. (See FIG. 1). For example, full spectrum (e.g. white) light is used to illuminate an examination substrate. Thereafter, the light reflected by the examination substrate 16 may be captured and the spectral characteristics thereof may be examined to measure a variety of characteristics of the examination substrate 16, including, without limitation, hemoglobin saturation and hematocrit concentration. Exemplary RFS image processors 72 include, without limitation, CCD and CMOS chips and photo-multiplier devices coupled to processors and display monitors. As such, the spectrophotometer 70 is in optical communication with the light transport section 14. In one embodiment, an RFS optics suite 74 may be used to process and refine the light received from the light transport section 14. Exemplary components which may be used within the RFS optics suite 74 include, without limitations, mirrors, positive lenses, negative lenses, acromats, compound lenses, astigmats, windows, flats, adaptive optics, holographical optical elements, spatial filters, pinholes, collimators, stages, wavelength filters, emission filters, and beam splitters.

As shown in FIG. 2, the fluorescence imaging module 34 includes a fluorescence imaging system 90 and a fluorescence image capture device 92. Exemplary fluorescence imaging systems 90 may include variety of optical components including, without limitation, microscopes, filter wheels, shutters, and optical filters. For example, green, yellow, and clear optical filters may be included. In one embodiment, the fluorescence imaging system 90 is configured to detect fluorescence from ultraviolet (UV) to infrared (IR) wavelengths. The fluorescence image capture device 92 may include a variety of devices including, without limitation, CCD chips and photomultiplier devices. Optionally, the fluorescence imaging module 34 may include a fluorescence optical suite 94 to refine or otherwise alter the light entering the fluorescence module 34. Exemplary components which may be used within the fluorescence optical suite 94 include, without limitations, mirrors, positive lenses, negative lenses, acromats, compound lenses, astigmats, windows, flats, adaptive optics, holographical optical elements, spatial filters, pinholes, collimators, stages, wavelength filters, emission filters, and beam splitters.

Referring again to FIG. 2, a beam director 98 may be included within or proximate to the analyzing section 12 and configured to direct light from the light transport section 14 to the OPS imaging module 30, the reflectance spectrophotometry module 32, and/or the fluorescence imaging module 34. Exemplary beam directors 98 include, without limitation, mirrors including dichroic mirror or elements and dark field mirrors, beam splitters, optical switches, movable or spinning geometric mirrors, corner cubes, prisms, and optical gratings. For example, in one embodiment the beam director 98 comprises a beam splitter directing fifty percent of the incoming light to the OPS imaging module 30 and 50 percent of the incoming light to the reflectance spectrophotometry module 32. In an alternate embodiment, the beam director 98 comprises a mirror having a non-reflecting area formed thereon, thereby reflecting a portion of light to the spectrophotometer and permitting dark field illumination to the OPS imaging module 30 and/or fluorescence imaging module 34. Optionally, the beam director 98 may comprise a spinning or moving mirrored polygon configured to reflect light from the light transport section 14 to the OPS imaging module 30, the reflectance spectrophotometer module 32, and/or the fluorescence imaging module 34. In another embodiment, the beam director 98 may be selectively actuated by the user to direct light to at least one of the OPS imaging module 30, the reflectance spectrophotometer module 32, the fluorescence imaging module 34, and/or any additional modules 34 coupled to or in optical communication with the analyzing section 12.

In one embodiment of the imaging system 10, the OPS imaging module 30 is coupled to the light transport section 14, while the reflectance spectrophotometer module 32 and/or the fluorescence imaging module 34 are positioned external to the imaging system 10 in optical communication therewith. A beam director 98 is positioned within the OPS module 30 and configured to direct a percentage (e.g. fifty percent) of the light received by the analyzing section 12 along an optical path to the reflectance spectrophotometer module 32 and the fluorescence imaging module 34, while the remaining light is directed to the OPS imaging module 30. An external beam director (not shown) may be used to further divide the directed light between the reflectance spectrophotometer module 32 and the fluorescence imaging module 34.

Figure 3:
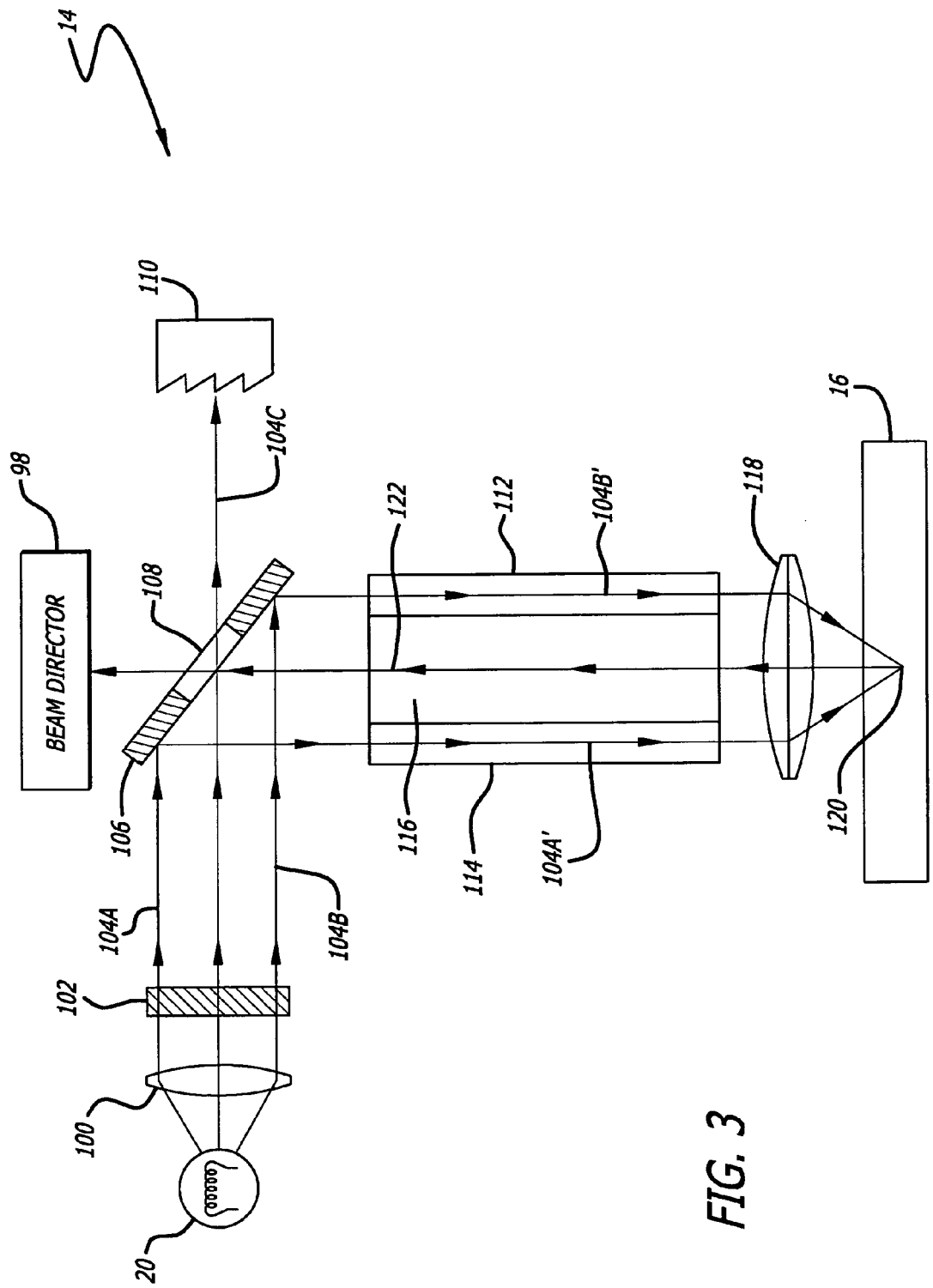
FIG. 3 shows a schematic diagram of an embodiment of a light transport section configured to project light on and receive reflected light from an examination substrate.

FIGS. 1 and 3 show an embodiment of a light transport section 14 of an imaging system 10. In the illustrated embodiment, the light source 20 is positioned proximate to a first lens 100. A variety of light sources may be used to illuminate the examination substrate 16, including, without limitation, incandescent lamps, gas discharge lamps, dye lasers, solid state devices such as light emitting diodes, laser diodes, gas lasers, excimer lasers, solid states lasers, and chemical lasers. For example, in one embodiment the external light source 20 comprises an incandescent lamp configured to irradiate the examination surface 16 with white light. In an alternate embodiment, the external light source 20 comprises a mercury lamp thereby stimulating fluorescence in the tissue of the examination substrate 16. In still another embodiment, the light source 20 comprises one or more LEDs configured to illuminate the examination substrate 16 with light of a discreet wavelength. In still another embodiment, the light transport section 14 may include a number of light sources. For example, a white light source and a UV light source could be used simultaneously. When using multiple light sources a shutter or beam splitter may be used to operate the system with a desired light source. For example, to operate the system using the white light source a shutter could be positioned to prevent the UV light from entering the light transport section 14. Thereafter, the user may actuate the shutter to illuminate the examination substrate 16 with the UV light rather than white light. In an alternate embodiment, a laser source may be coupled to or in optical communication with the imaging system 10 to treat the examination substrate 16. For example, the laser source may be used to treat microcirculatory disorders including, without limitation, cancerous tissue, skin discolorations, and/or tissue lesions. Optionally, the imaging system 10 may be operated without a first lens 100.

Referring again to FIGS. 1 and 3, light emitted by the external light source 20 is incident on a polarizer 102 configured to polarize light to a desired orientation. Thereafter, polarized light rays 104A, 104B, and 104C are incident on a light director 106 configured to direct light rays 104A', and 104B' to the examination substrate 16. In the illustrated embodiment, the light director 106 includes a non-reflective or dark field spot 108 formed thereon, thereby permitting light ray 104C to proceed therethrough and be absorbed by a beam dump or absorber 110. Exemplary light directors include, without limitation, beam splitters, dichroic junctions, and mirrors.

A light guide 112 in optical communication with the light source 20 receives and transmits light rays 104'A, 104B' to the examination substrate 16. In the embodiment illustrated in FIG. 3, the light guide 112 includes an illumination segment 114 and a reflectance segment 116. The illumination segment 114 transmits light to the examination substrate 16 for illumination, while the reflectance segment 116 transmits reflected light from the examination substrate 16 to the beam director 98 of the analyzing section 12. Exemplary light guides include, for example, boroscopes, endoscopes, liquid light guides, polymer light guides, glass light guides, tubular bodies, and single or bundled optical fibers. For example, FIGS. 4A-4D show several embodiments of light guides 112 which may be used with in the light transport section 14. As shown in FIG. 4A, the light guide 112 may include polymer illumination and reflectance segments 114, 116, respectively. The reflectance segment 116 may be optically isolated from the illumination segment 114, for example, by an internal cladding 115. Similarly, the illumination segment 114 may include an external cladding 117 thereon. As shown in FIG. 4B, the reflectance segment 116 may be comprised of a bundle of optical fibers while the illumination segment 114 comprises a polymer light guide. In the alternative, FIG. 4C shows a light guide 112 having an illumination segment 114 constructed of a bundle of optical fibers and having a polymer reflectance segment 116 therein. FIG. 4D shows another embodiment wherein the illumination segment 114 and the reflectance segment 116 are constructed from a bundle of optical fibers.

As shown in FIG. 3, a lens or lens system 118 may be included within the light transport section 14 to focus the light rays 104A', 104B'. The focal point 120 of the lens system 118 may be located above, at the surface of, or below the surface of the examination substrate 16. Optionally, the lens system 118 may include a reflector or other device configured to project illuminating light at any angle relative to the longitudinal axis of the light transport body 14. For example, the lens system 118 may permit a user to project light at an angle of about 90 degrees relative to the longitudinal axis of the light transport body 14. As shown, the distal tip 137 of the light transport body 14 is positioned a distance D from the examination substrate 16. As a result, the light transport body 14 does not contact the examination substrate 16 thereby permitting the unimpeded flow of material through the examination substrate 16. As such, the imaging system 10 permits the user to measure the flow of a material through the examination substrate 16 in real time. Light 122 reflected from the examination substrate 16 is captured by the lens 118 and transmitted through the reflectance segment 116 and the dark field spot 108 of the light director 106 to the beam director 98 analyzing section 12. Optionally, a polarizer (not shown) may be positioned proximate to the distal tip 137 of the light transport body 14 and configured to polarize light prior to illuminating the examination substrate 16.

FIG. 5 shows an alternate embodiment of a light transport section 14. As shown, an internal light source 18 may be used to illuminate the examination substrate 16. For example, one or more LEDs may be used to illuminate an examination substrate 16 with a discreet wavelength of light. In an alternate embodiment, the internal light source 18 may comprises LEDs of different color, thereby illuminating the examination substrate 16 with light of multiple discreet wavelengths or with full spectrum light for additional treatment (e.g. laser ablation). Multiple wavelength LED's can also be used to generate images of the distribution of Hb saturation in an SDF imaging modality. Those skilled in the art will appreciate that the use of LEDs as a light source enables the imaging system 10 to be powered by a battery or other low-power power supply relative to previous systems. For example, the imaging system 10 may be powered by coupling the imaging system 10 to a universal serial port of a personal computer. One or more internal lenses 130 may, but need not be, included within the light transport section 14 and positioned proximate to the internal light source 18. Similarly, one or more optical polarizers or filters 132 may be positioned proximate to the internal lenses 130. The internal light sources 18 emit rays 134A, 134B which are transmitted to the examination substrate 16 by the illumination segment 136 of the light guide 138. An examination lens system 140 may be used to focus the light rays 134A, 134B to the examination substrate 16. A focal point 142 of the lens system 140 may be located above, at the surface of, or below the surface of the examination substrate 16. Thereafter, light rays 144 reflected by the examination substrate 16 are collected by the lens system 140 and transmitted to the beam director 98 of the analyzing section 12 by the reflectance segment 146 formed within the light guide 138.

Figure 6:
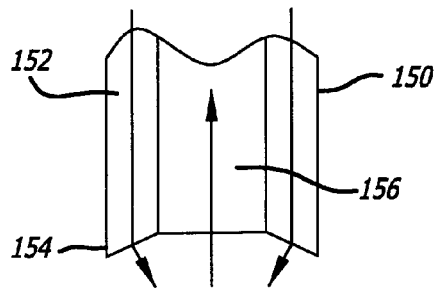
FIG. 6 shows a side view of an alternate embodiment of a light transport body of a light transport section.

FIG. 6 shows an alternate embodiment of a light guide 150. As shown, the light guide 150 includes an illuminating segment 152 having a focused or curved distal tip 154, thereby directing light rays to a focal point within an examination substrate (not shown). The reflectance segment 156 is configured to transmit light from the examination substrate 16 to the analyzing section 12 (See FIG. 1).

Figure 7:
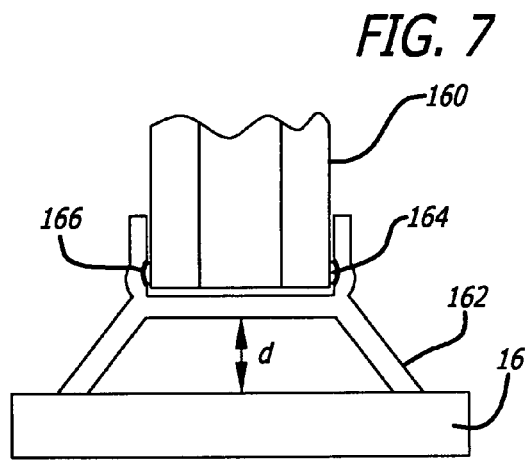
FIG. 7 shows side view of an embodiment of a spacer device coupled to an embodiment of a light transport body.
Figure 8:
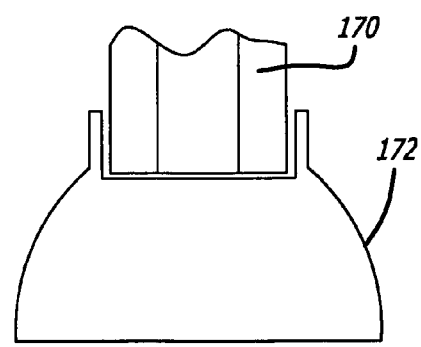
FIG. 8 shows a side view of another embodiment of a spacer device coupled to an embodiment of a light transport body.

FIGS. 7 and 8 show embodiments of spacer devices which may be affixed to the distal end or distal section of the light guide. FIG. 7 shows a light guide 160 having a spacer 162 attached thereto. In the illustrated embodiment, the distal section of the light guide 160 may include one or more lock members 164 thereon to securely couple the spacer 164 to the light guide 160. As such, the spacer 160 may include a locking member recess 166 to accommodate the locking members 164. The spacer 162 ensures that the light guide 160 remains at least a distance d from the examination substrate 16. FIG. 8 shows an alternate embodiment of a spacer 172 coupled to a light guide 170. The spacers 162, 172 may be manufactured from a variety of materials including, without limitation, plastic, rubber, elastomer, silicon, or any other biologically compatible material. In one embodiment, the spacer 162, 172 are disposable.

Figure 9:
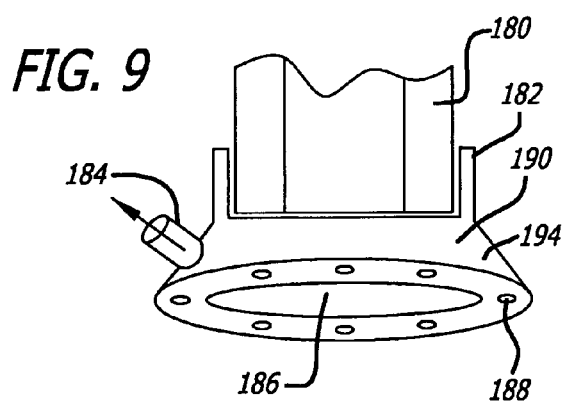
FIG. 9 shows a side view of an embodiment of a spacer device configured to couple to an examination substrate coupled to an embodiment of a light transport body.
Figure 10:
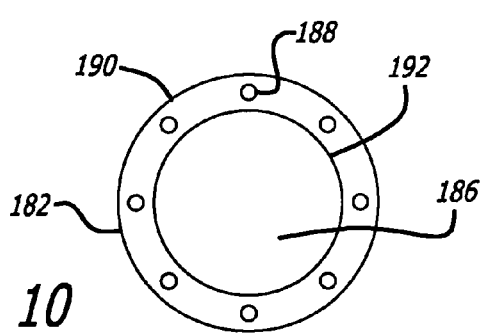
FIG. 10 shows a bottom view of an embodiment of the spacer device shown in FIG. 9.

FIGS. 9 and 10 show an embodiment of a light guide 180 having an alternate embodiment of a spacer 182 attached thereto. The spacer 182 includes a vacuum port 184 attachable to a source of vacuum (not shown). The spacer 182 includes a spacer aperture 186 for irradiating the examination substrate (not shown). The spacer 182 includes one or more attachment orifices 188 thereon which are in communication with the vacuum port 184. The attachment orifices 188 are formed between an exterior wall 190 and an interior wall 192 of the spacer body 194 and are isolated from the spacer aperture 186. As such, the spacer 180 is configured to couple to the examination substrate (not shown) when the vacuum source is actuated without adversely effecting the irradiation of the examination surface. As such, the spacer 180 may be rigid or, in the alternative, may be constructed of a compliant material for use within or on compliant organs or structures. Like the embodiments described above, the spacer 182 may be manufactured from a variety of materials and may be disposable. One or more additional ports may be formed on the spacer body 194 for the administration of medicinal or therapeutic agents.

Figure 11:
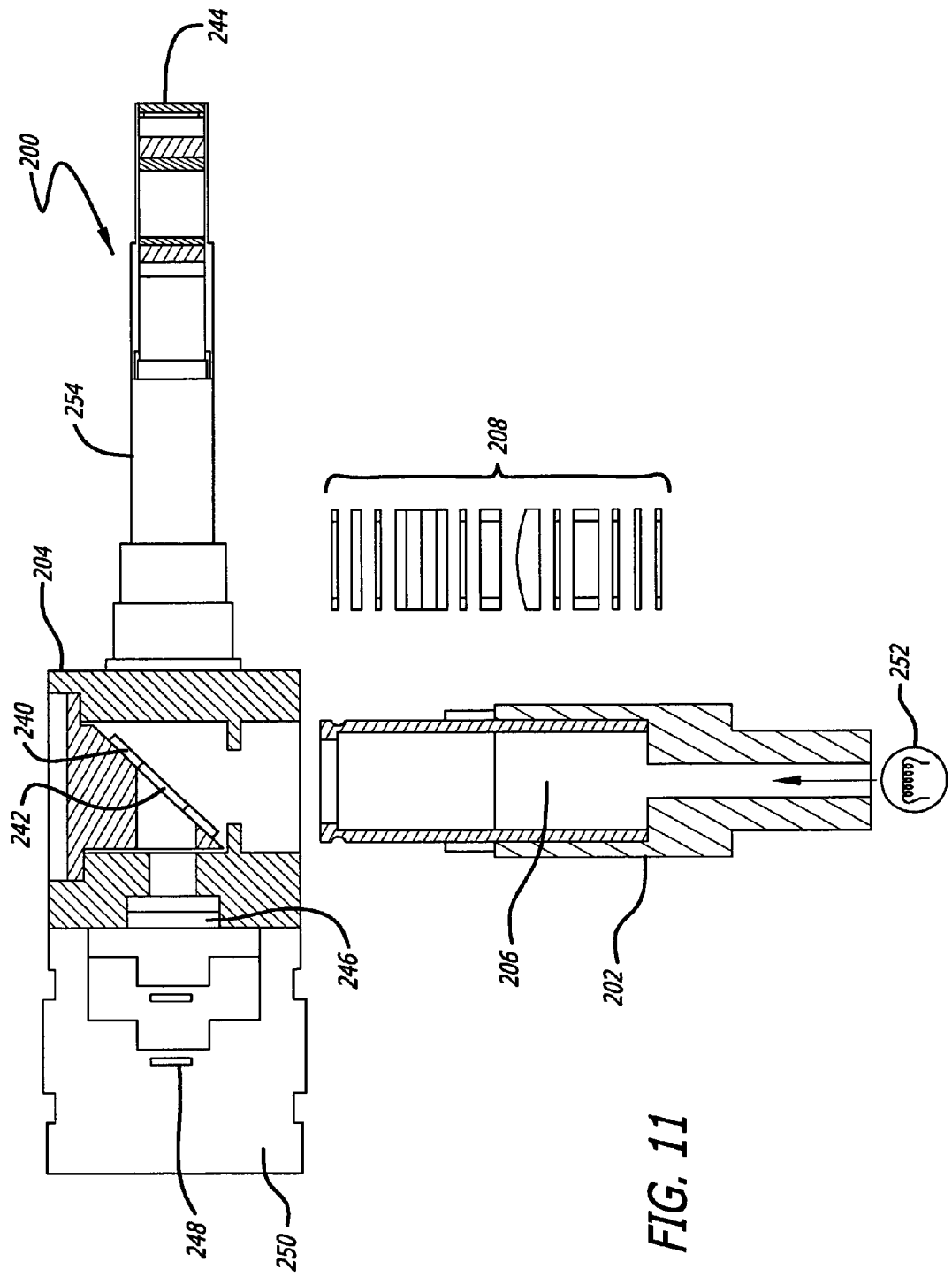
FIG. 11 shows a cross sectional view of an embodiment of an imaging system for analyzing reflected light.
Figure 12:
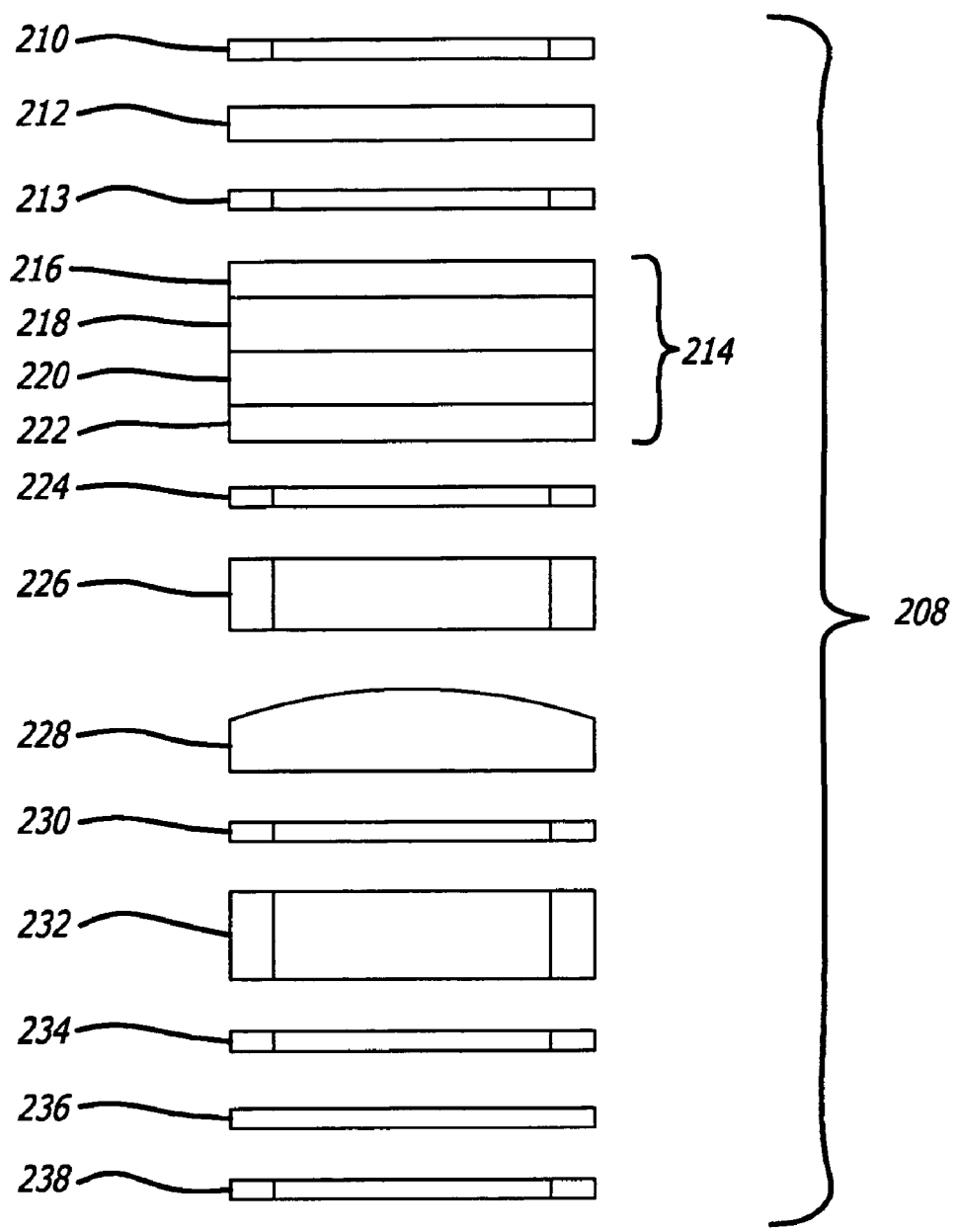
FIG. 12 shows a side view of an optical system for use in the an imaging system for analyzing reflected light shown in FIG. 10.

FIGS. 11 and 12 show an embodiment of an imaging system 200. As shown, the imaging system 200 includes an illumination body 202 and a reflectance body 204. The illumination body 202 defines an optics recess 206 configured to receive an optical system 208 therein. The optical system 208 includes a first spacer 210, a first dark field mirror 212, a filter spacer 213, and a filter bank 214. In the illustrated embodiment, the filter bank 214 includes a clear filter 216, a yellow filter, 218, a green filter 220, and a white filter 222. A second spacer 224 is positioned proximate to the filter bank 214. A third spacer 226 is positioned between the second spacer 224 and a lens 228. A fourth, fifth, and sixth spacers 230, 232, and 234, respectively, are positioned proximate thereto. A second dark field filter 236 is positioned between the sixth spacer 234 and the seventh spacer 238.

Referring again to FIG. 11, the reflectance body 204 includes a light director 240 therein. The light reflector 240 includes a non-reflective area 242 formed thereon. In addition, the reflectance body 204 includes an examination tip 244 which is configured to be positioned proximate to the examination substrate (not shown). A polarizer and/or filter 246 and an image capture device 248 may be positioned within the analyzing section 250 of the reflectance body 204. During use, a light source 252 projects light which is filtered and focused by the optical system 208 located within the illumination body 202. The light from the light source 252 is directed by the light director 240 to the examination substrate (not shown) located proximate to the examination tip 244. Light reflected by the examination substrate (not shown) is transmitted to the analyzing section 250 by the light guide 256, where the light is depolarized and analyzed.

Figure 13:
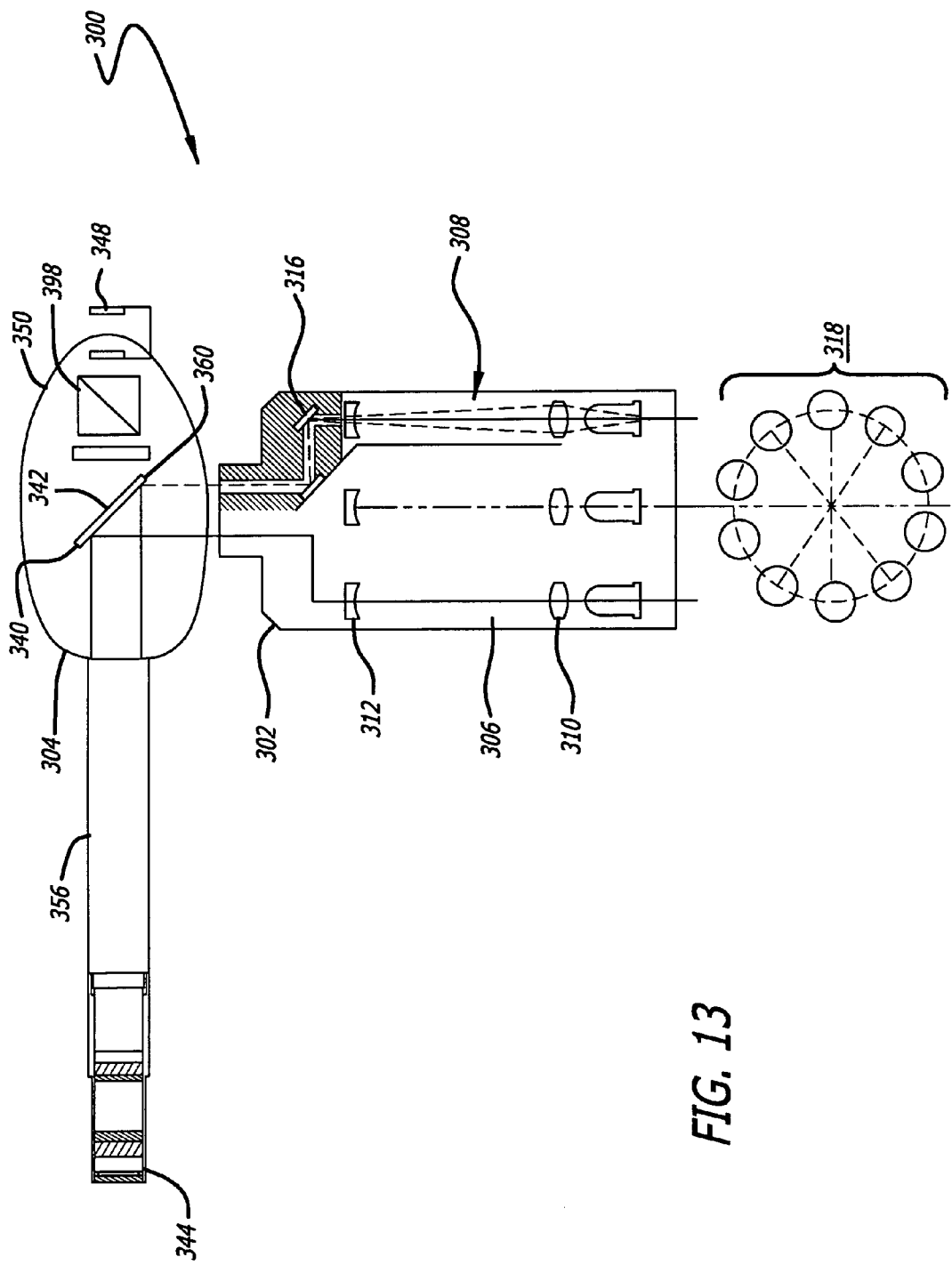
FIG. 13 shows a cross sectional view of an embodiment of an imaging system for analyzing reflected light having an internal light source positioned therein.

FIG. 13 shows another embodiment of an imaging system. As shown, the imaging system 300 includes an illumination body 302 and a reflectance body 304. The illumination body 302 defines an optics recess 306 configured to receive an optical system 308 therein. The optical system 308 includes a first lens 310 and a second lens 312. Positioned proximate to the first lens 310 is an internal light source 318. In the illustrated embodiment, the internal light source 318 comprises a number of LEDs configured to project light through the optical system 308. One or more reflectors 316 may be used to ensure that the light is transmitted through the illumination body 302.

As shown in FIG. 13, the reflectance body 304 includes a light director 340 therein. The light reflector 240 includes a non-reflective area 342 formed thereon. In addition, the reflectance body 304 includes an examination tip 344 which is configured to be positioned proximate to the examination substrate (not shown). A beam director 398 and an image capture device 348 may be positioned within the analyzing section 350 of the reflectance body 304. During use, the light source 318 projects light which is focused by the optical system 308 located within the illumination body 302. The light from the light source 318 is directed by the light director 340 to the examination substrate (not shown) located proximate to the examination tip 344. Light reflected by the examination substrate (not shown) is transmitted to the analyzing section 350 by the light guide 356, where the light is analyzed. As shown, the analyzing section 350 may include one or more filters or polarizers 360 therein.

Figure 14:
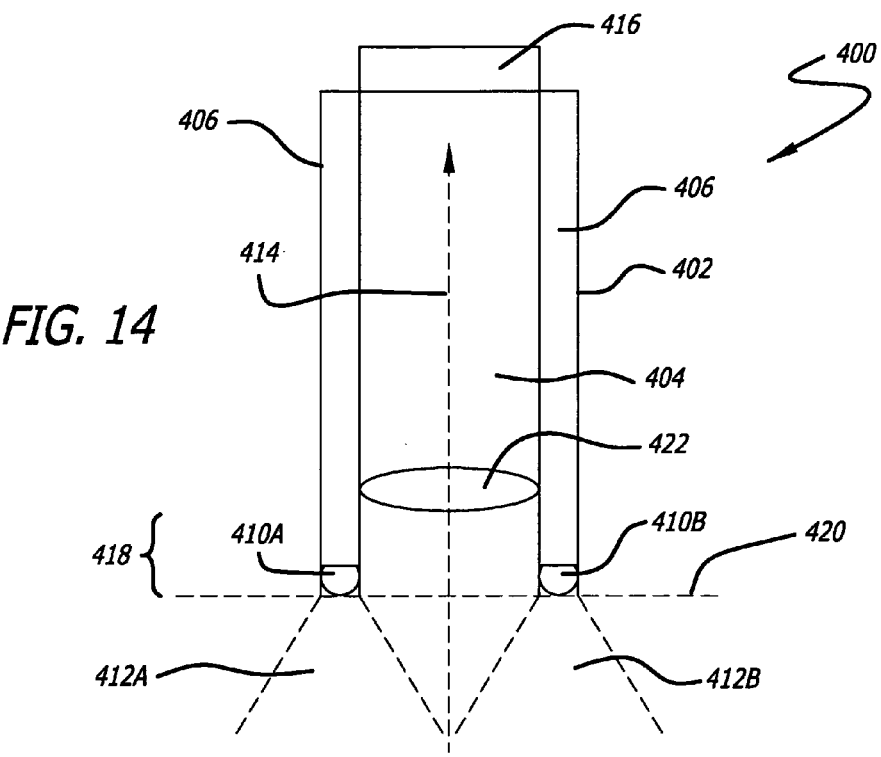
FIG. 14 shows a side cross-sectional view of an embodiment of an imaging system configured to permit side stream dark field imaging of an area.
Figure 15:
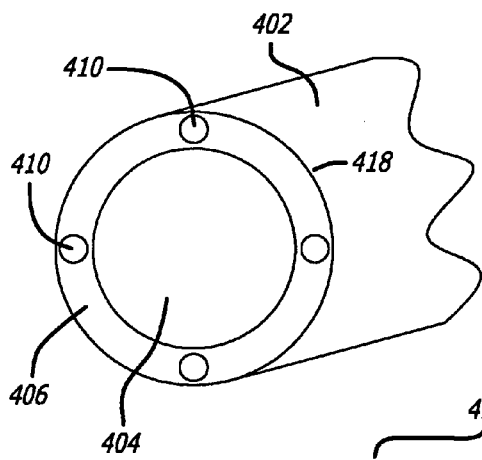
FIG. 15 shows a perspective view of the distal portion of an embodiment of the imaging system shown in FIG. 14.

As shown in FIGS. 3-5, at least one light source may be used to illuminate structures located below the surface of a substrate. FIGS. 14 and 15 show alternate embodiments of imaging systems useful in imaging sub-surface structures while avoiding or reducing the effects of surface reflection. FIG. 14 shows an imaging system 400 comprising a body 402 having one or more imaging passages 404 formed therein. One or more illumination passages 406 may be formed within the body 402 and may be optically isolated from the imaging passage 404. In one embodiment, the body is rigid. In an alternate embodiment, the body 402 is flexible. For example, the body 402 may comprise a catheter body. Optionally, the body 402 may include an additional lumen formed therein. For example, an additional lumen may be positioned within the body 402 and may be used to deliver therapeutic agents to a treatment site. In another embodiment, an additional lumen may be used to deliver a vacuum force to a treatment site. In the illustrated embodiment, the illumination passage 406 is positioned radially about imaging passage 404. In the illustrated embodiment, the illumination passage 406 encircles the imaging passage 404. In an alternate embodiment, the illumination passage 406 may be positioned anywhere within the body 402. As shown, the illumination passage 406 is optically isolated from the imaging passage 404. Therefore, illuminating energy transported through the illumination passage 406 is prevented from entering the imaging passage 404. As such, the present systems permits side stream dark field imaging (hereinafter SDF). As shown in FIG. 14, a feature of SDF imaging is that the illuminated light 412A and 412B and the reflected light 414 travel via independent pathways. Thus, the illumination can be placed directly on the tissue and the observations can be made adjacent to it without light crossing over between two paths.

Referring again to FIG. 14, at least one illumination source may be positioned within the illumination passage 406. In one embodiment, the illumination source 410 comprises one or more LED's configured to project a selected wavelength to the substrate 420. In an alternate embodiment, the illumination source 410 comprises a plurality of LED's configured to project multiple wavelengths to the substrate 420. For example, as shown in FIG. 14 a first illumination source 410A configured to project light to the substrate 420 is positioned at the distal portion 418 of the body 402. Similarly, a second illumination source 410B is positioned at the distal portion 418 of the body 402. As such, the first and second illumination sources 410A, 410B are positioned proximate to the substrate 420 under examination. Optionally, any number of illumination sources may be positioned within the body 402. Exemplary illumination sources include, without limitation, LED's, LLED's, incandescent bulbs, laser light sources, etc.

FIG. 15 shows a perspective view of the distal portion of an alternate embodiment of the imaging device 400 shown in FIG. 14. As shown, the body 402 includes an imaging passage 404 and at least one illumination passage 406 optically isolated from the imaging passage 404. One or more illumination devices 410 are located within the illumination passage 406 and positioned proximate to the distal portion 418 of the body 402. As such, during use the illumination source are positioned proximate to the substrate 420.

Figure 16:
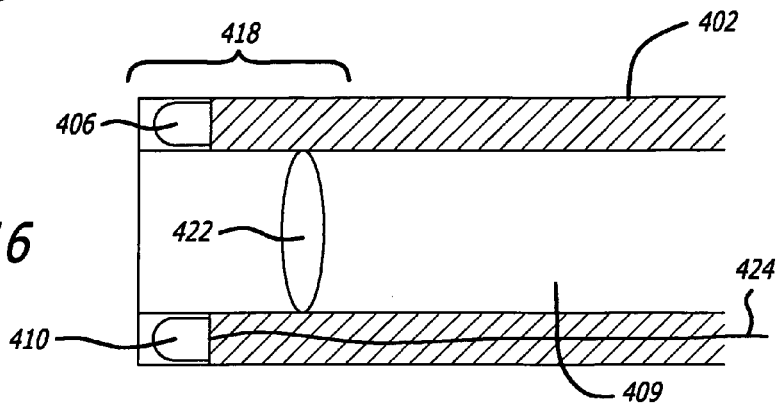
FIG. 16 shows a cross sectional view of an embodiment of an imaging system having one or more illumination sources located within illumination passages formed in a body.

FIG. 16 shows a cross sectional view of the distal portion of an embodiment of an imaging device. As shown, The body 402 defines an imaging passage 404 and an illumination passage 406 therein. Like the previous embodiments, the illumination passage 406 is optically isolated from the imaging passage 404. In the illustrated embodiment, the illumination passage 406 terminates proximate to the distal portion 418 of the body 402. Optionally, the illumination passage 406 may continue through the length of the body 402. As such, the illumination passage 406 may include one or more optical fibers configured to deliver illuminating energy to the substrate 420 from a remote location. In the illustrated embodiment, one or more illumination sources 410 are positioned within the illumination passage 406. For example, one or more LED's may be positioned within the illumination passage 406. Like the previous embodiments shown in FIGS. 14 and 15, the illumination passage 406 is optically isolated from the imaging passage 404. Optionally, at least one conduit 424 may traverse through the body 402 thereby coupling the illumination source 410 to a source of power. In the illustrated embodiment at least one lens 422 is positioned within the imaging passage 404 thereby transmitting an image received from a substrate 420 to an image capture device 416. (See FIG. 14). Optionally, the imaging system shown in FIGS. 14-16 may be used without a lens 422.

With reference to FIG. 14, during use, the first illumination source 410A projects illuminating energy 412A to the substrate 420. Similarly, the second illumination source 410B projects illuminating energy 412B to the substrate 420. As shown in FIG. 14, the illumination energies 412A, 412B are optically isolated from the imaging passage 404. The first and second illumination energies 412A, 412B may be the same or differing wavelengths. Further, as the first and second illumination sources 410A, 410B are positioned at the distal portion of the body 402 proximate to the substrate 420, surface reflections therefrom are reduced or eliminated. As shown, a subsurface image 414 is transported by the imaging passage 404 from the substrate 420 to an image capture device 416. Exemplary image capture devices include, without limitation, CCD devices, cameras, spectrophotometers, photomultiplier devices, analyzers, computers, etc. Optionally, one or more lenses 422 may be positioned within the image passage 404 or body 402 to focus illumination energy 412 to the substrate 420 or to assist in the transport of an image 414 from the substrate 420 to the image capture device 420416, or both. As stated above, the optical isolation of the illumination energy from the image received from the substrate reduces or eliminates the effects of surface reflections while enabling SDF imaging in addition to a variety of alternate imaging modalities or spectroscopic examination of an area.

Figure 17:
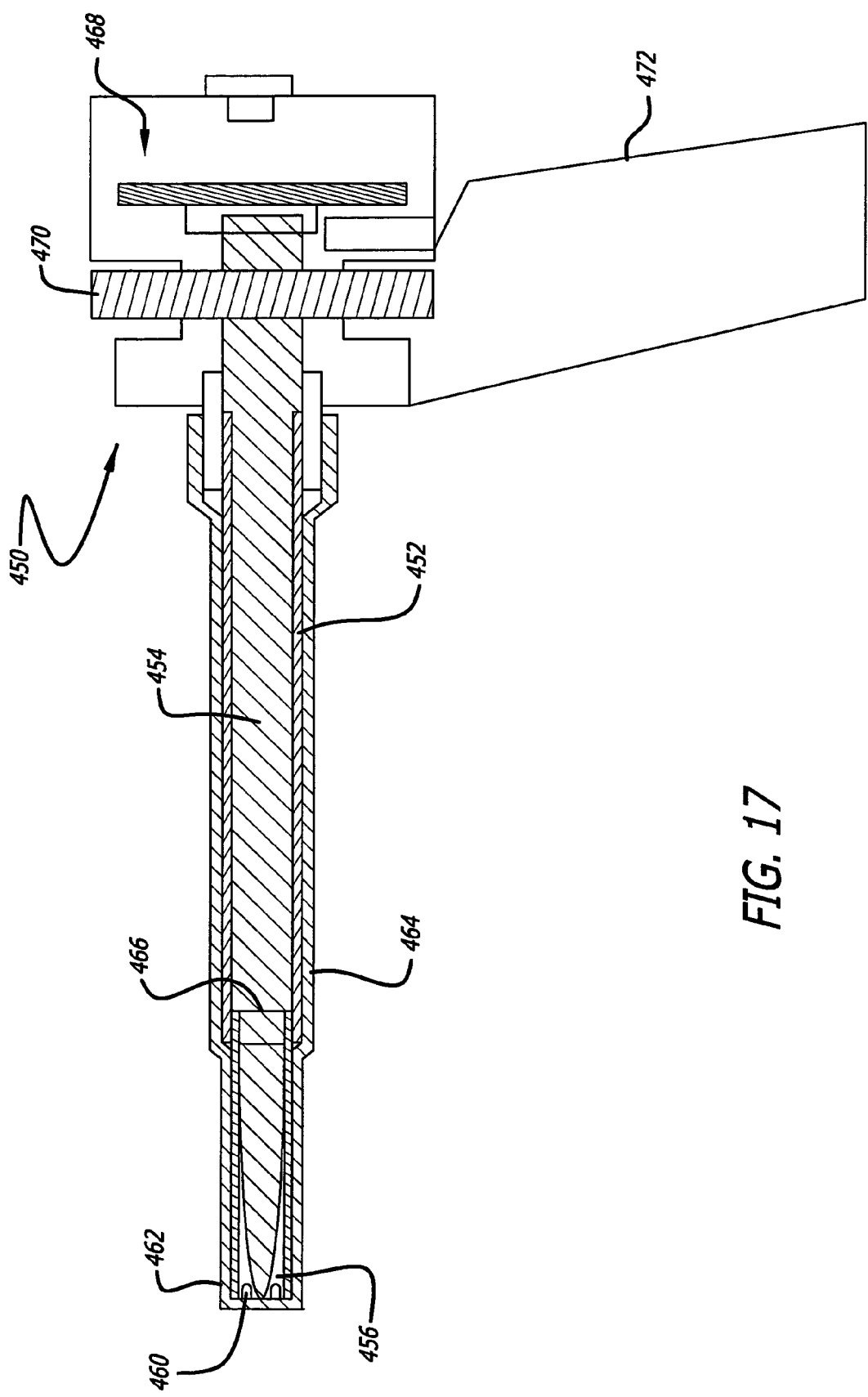
FIG. 17 shows a cross sectional view of an embodiment of an imaging system having a body coupled to handle portion.

FIG. 17 shows an alternate embodiment of an SDF imaging system. As shown, the SDF imaging system 450 comprises a body 452 defining an imaging passage 454 and an illumination passage 456 optically isolated from the imaging passage 454. The illumination passage 456 includes one or more illumination sources 460 therein. Exemplary illumination sources 460 include, without limitation, LED's, LLEDs, and incandescent bulbs. As shown, the illumination sources 460 are located proximate to the distal portion 462 of the body 452. Optionally, the illumination sources 460 may be located some distance from the examination area. As such, illuminating energy may be transported to the examination area through fiber optic conduits positioned within the body 452. Like the previous embodiments, the body 402 may be rigid or flexible. In the illustrated embodiment, a cap device 464 is positioned over the body 452. In one embodiment, the cap device 464 may comprise an optically transparent disposable cap device 464 configured to be detachably coupled to the body 452. During use the cap device 464 may protect the body 402 from biological materials and contaminants. As such, the cap device 464 may be sterile.

Referring again to FIG. 17, at least one lens 466 may be positioned within the imaging passage 454. The imaging passage 454 is in optical communication with an imaging capture device 468. The image capture device 468 may comprise any of devices useful in capturing and analyzing an image received from a substrate. For example, the image capture device 468 may comprise a CCD device, photomultiplier, computer, spectrophotometer, and the like. Further, a focusing device 470 may be included within the body 452 or the image capture device 468. Exemplary focusing devices include, without limitation, additional lenses, mechanical drives or positioners, and the like. Optionally, the SDF imaging system 450 may further include a handle 472 to assist a user in positioning the device. Further, the SDF imaging system 450 may be configured to be coupled to a computer, power source, etc.

Figure 18:
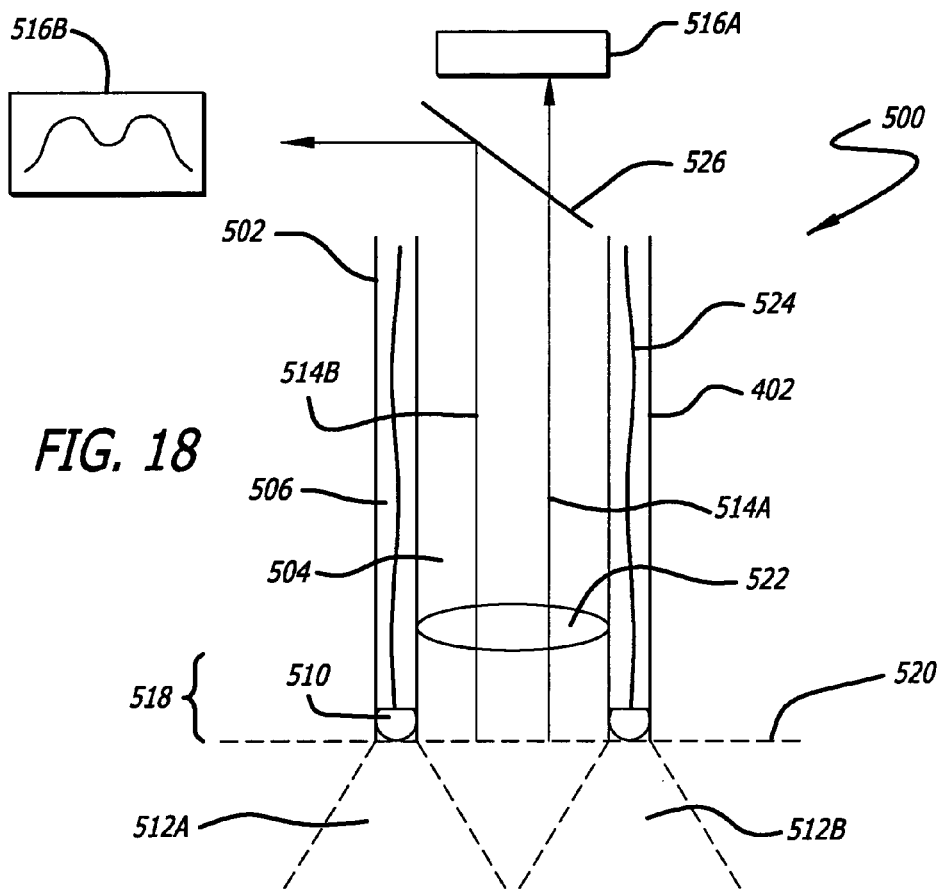
FIG. 18 shows a schematic diagram of an embodiment of an imaging system for projecting light to a substrate and collecting light therefrom for analysis.

FIG. 18 shows an alternate embodiment of an imaging system. As shown, the imaging system 500 includes a body 502 defining an imaging passage 504 and at least one illumination passage 506 optically isolated from the imaging passage 504. The illumination passage 506 includes one or more illumination sources 510 therein. As shown, the illumination sources 510 are located proximate to the distal portion 518 of the body 502, however, the illumination source may be located anywhere on the body 502. Optionally, a cap device (not shown) may be positioned over the body 502. For example, the cap device (not shown) may comprise an optically transparent disposable device configured to be detachably coupled to the body 502.

Referring again to FIG. 18, at least one lens 522 may be positioned within the imaging passage 504. The imaging passage 504 is in optical communication with at least one image capture device 516. In the illustrated embodiment, a first image capture device 516A and a second image capture device 516B may be used with the system. Further, one or more optical modulators 526 may be positioned within the image passage 504 and configured to modulate imaging signals from the substrate 520. exemplary optical modulators 526 include, without limitation, mirrors, band pass plates, polarizers, gratings, and the like. The image capture devices 516A, 516B may comprise any number of devices useful in capturing and analyzing an image received from a substrate. For example, the image capture devices 516A, 516B may comprise CCD devices, spectrophotometers, spectrum analyzers, and the like.

Figure 19:
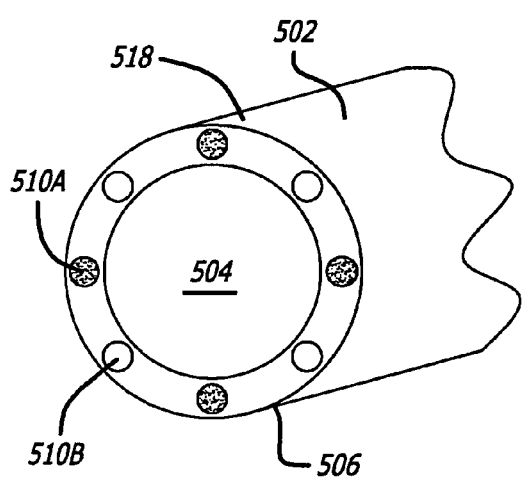
FIG. 19 shows a perspective view of the distal portion of the imaging system shown in FIG. 18.
Figure 20:
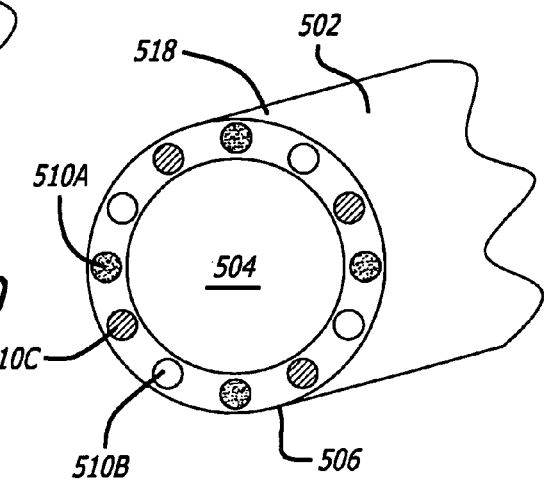
FIG. 20 shows a perspective view of the distal portion of another embodiment of imaging system shown in FIG. 18.

As shown in the FIGS. 18 and 19, the illumination sources 510 may comprise LED's of a single wavelength. In the alternative, the illumination sources 510 may be configured to irradiate light of multiple wavelengths. For example, FIG. 19 shows a device having a first illumination source 510A irradiating at a first wavelength and a second illumination source 510B irradiating at a second wavelength. FIG. 20 shows a device having a first illumination source 510A, a second illumination source 510B, and a third illumination source 510C, each illumination source irradiating at a different wavelength. As such, the system may be configured to perform a number of imaging and analyzing procedures with a single device. For example, a first wavelength may be projected to the substrate and used for SDF microcirculation imaging within the underlying vasculature, while a second wavelength may be projected to the substrate and used for detecting oxygen saturation within a blood flow. In short any number of wavelengths of illuminating energy may be projected from the illumination sources 510 and used for any number of analytical processes. For example, the imaging system 500 may be configured to permit imaging of the microcirculation and spectroscopic examination of an area with a single device.

Figure 21:
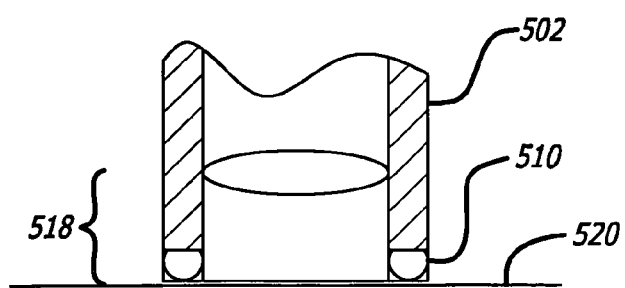
FIG. 21 shows a side cross sectional view of an embodiment of an imaging system wherein the distal portion thereof is in contact with an examination substrate.
Figure 22:
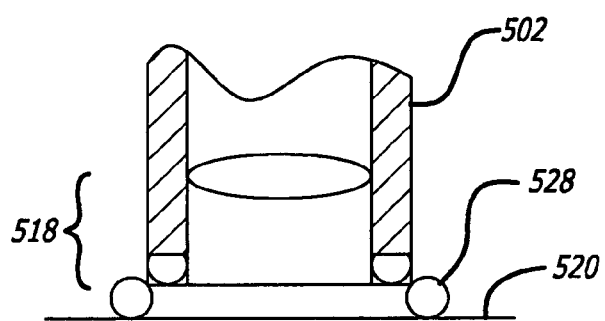
FIG. 22 shows a side cross sectional view of an embodiment of an imaging system wherein the distal portion includes an engaging device thereon.
Figure 23:
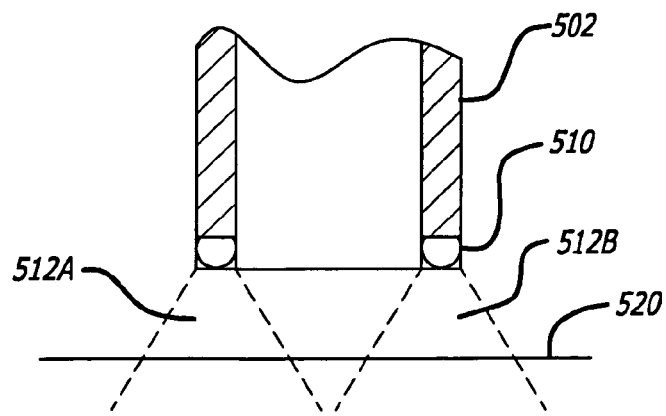
FIG. 23 shows a side cross sectional view of an embodiment of an imaging system wherein the distal portion is not in contact with the examination substrate.

Referring to FIGS. 18 and 21, during use the distal portion 518 of the body 502 may be in contact with the substrate 520 under examination. As such, the illumination source(s) 510 may be positioned in close proximity to the substrate 520. Optionally, the distal portion 518 may include one or more engaging devices 528 coupled to the body 504 or the cap device (not shown). For example, as shown in FIG. 22, the engaging device 528 may comprise an inflatable device configured to dissipate a pressure applied to the substrate 520 by the distal portion 518 of the body 502. In an alternate embodiment, shown in FIG. 23, the distal portion 518 may be positioned proximate to, but not in contact with, the substrate 520. As such, the illumination sources 510 may be configured to project illuminating energy 512A, 512B to the substrate 520. Optionally, one or more lenses may be in optical communication with the illumination source(s) 510 to aid in the projection of illumination energy 512A, 512B to the substrate 520.

Figure 24:
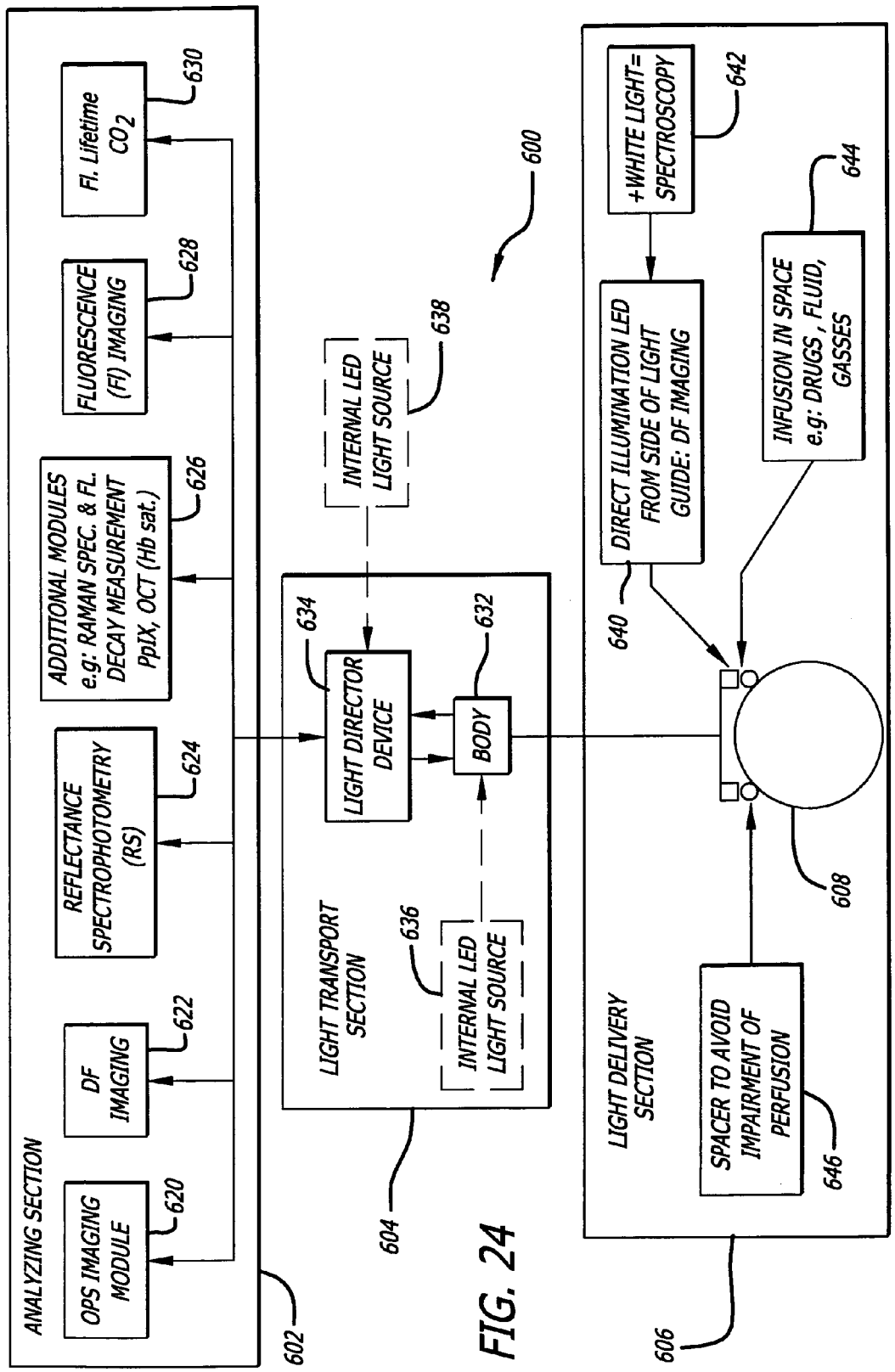
FIG. 24 shows a block diagram of diagram of an embodiment of an imaging system for imaging microcirculation within a structure and analyzing light reflected from an examination substrate.

FIG. 24 shows a block diagram of an embodiment of an imaging and analyzing system. As shown, the imaging system 600 includes an analyzing section 602, a light transport section 604, and a light delivery section 606 configured to deliver light to and receive information from a substrate 608. As stated above, the analyzing section 602 may include any number of analyzing modules configured to process information received from the substrate 608. In the illustrated embodiment, the analyzing section 602 includes an OPS imaging module 620, a dark filed illumination module 622, a reflectance spectrophotometry module 624, an additional processor module 626, a fluorescence module 628, and/or a fluorescence lifetime module 630. The additional processor module 626 may include one more processing module including, without limitation, Raman spectroscopy devices, fluorescence decay processors, PPIX analyzers, and/or OCT (Hb sat) analyzers, and/or $CO_2$ analyzers. Referring to FIGS. 18 and 21, the analyzing section 602 may be configured to receive imaging information from the substrate 520 via the imaging passage 504 formed within the body 502. Those skilled in the art will appreciate that the present system enables a user to selectively analyze a substrate using multiple imaging modalities, spectrophotometry modalities, and similar analyzing methods using a single device coupled to multiple analyzers.

The light transport section 604 may comprise a body 634 configured to transport light to and from the substrate 608. For example, the body 634 may include an image passage 504 and an optically isolated illumination passage 506 as shown in FIG. 18. Further, the light transport section 604 may include one or more internal illumination sources 636 positioned therein and configured to irradiate the substrate 608. Optionally, one or more optical elements 634 may be positioned within the body 632. Further, the body 632 may be configured to receive and transport light from an external light source 638 to the substrate 608.

Referring again to FIG. 24, the light delivery section 606 may comprise a direct illumination source 640 configured to be positioned proximate to the substrate 608 and providing direct illumination thereto. As such, the direct illumination source 640 is optically isolated from an image received from the substrate 608. Exemplary direct illumination sources 640 include LLED's, LED's, and the like. Further, one or more white light illumination sources 642 may be used to illuminate the substrate 608. In one embodiment, the light delivery section 606 may be configured to deliver materials to or receive materials 644 from the substrate 608. For example, the light delivery section 606 may be configured to infuse therapeutic agents to the substrate 608. Optionally, the light delivery section 606 may include one or more engaging devices 646 positioned thereon to assist in positioning the system during use.

Figure 25:
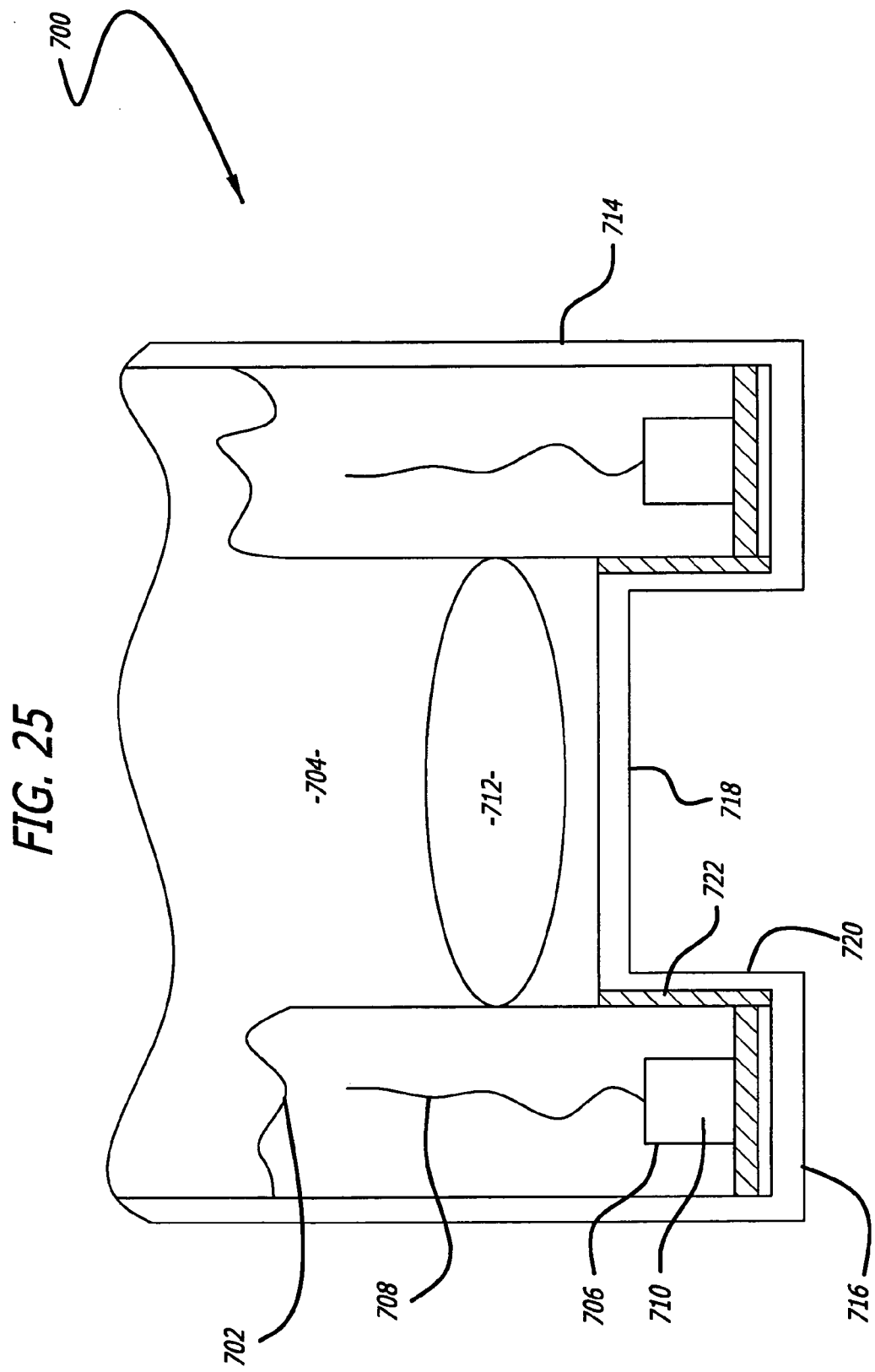
FIG. 25 shows a cross sectional view of an embodiment of a cap device which may be affixed to a body of an imaging system.

As stated above, the preceding imaging and analyzing systems disclosed herein may include one or more cap devices 464 which may be detachably coupled to the body 452. (See FIG. 17). Generally, the cap device 464 may comprise optically transparent materials configured to protect the body 452 during use. As such, the cap device 464 may be disposable. FIG. 25 shows an alternate embodiment of a cap device 714. As shown in FIG. 25, the imaging device 700 includes a body 702 having an imaging passage 704 and an illumination passage 706 optically isolated from the imaging passage 704 formed therein. The illumination passage 706 may include one or more conduits 708 coupled to one or more illumination sources 710 located therein. As shown in FIG. 25, one or more lenses 712 may be positioned within the imaging passage 704. A cap device 714 may be coupled to the body 702. The cap device 714 includes an illumination field 716 optically isolated from an imaging relief 718. In the illustrated embodiment, the illumination field 716 is positioned proximate to the illumination sources 710 located within the body 702. Similarly, the imaging relief 718 is positioned proximate to the imaging passage 704. At least one isolation surface 720 optically isolates the illumination field 716 from the imaging relief 718. For example, in the illustrated embodiment the isolation surface 720 include a reflective foil 722 thereon which is configured to prevent light from illumination sources 710 from directly entering the imaging passage 704 without first engaging a substrate under examination. Alternate isolation materials may be used on the isolation surface 722 including, without limitation, dyes, foils, impregnations, etc. Optionally, the cap device 714 may be disposable and may be configured to detachably couple to the body 702.

Figure 26:
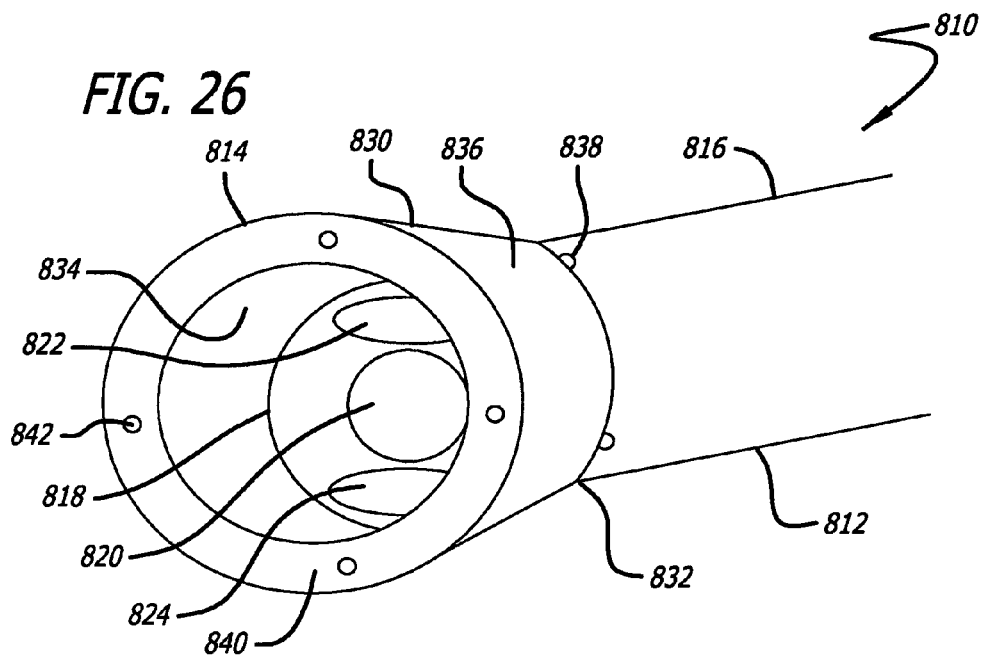
FIG. 26 shows a perspective view of embodiment of an imaging system configured for sub-surface imaging of an area.

FIG. 26 shows yet another embodiment of a reflectance avoidance imaging system. As shown, the reflectance avoidance imaging system 810 includes an imaging device 812 having a spacer or tissue engaging tip 814 attached thereto. The imaging device 812 includes a body 816 having a distal portion 818 configured to receive and engage the spacer 814. In one embodiment, the spacer 814 is detachably coupled to the body 816. Optionally, the spacer 814 may be non-detachably coupled to the body 816.

Referring again to FIG. 26, the imaging body 816 includes one or more conduits formed therein. In the illustrated embodiment, the body 816 includes an imaging conduit 820 configured to project light from a light source (not shown) to a work surface. In addition, the imaging conduit 820 collects light reflected from the work surface and transports the reflected light to a sensor suite (not shown) in communication therewith. Exemplary sensor suites include, without limitation, a CCD or any other type of imaging or sensing device, spectral photometers, and the like. Optionally, a secondary imaging conduit 822 may be positioned within the body 816. For example, the secondary imaging conduit 822 may be configured to measure $CO_2$ within tissue through the use of a $CO_2$ sensing dye. The $CO_2$ sensing dye enables the measurement of fluorescence decay and may utilize light received from and transmitted through the imaging conduit 820. Optionally, one or more additional conduits 824 may be positioned within the body 816. For example, any number of fluid conduits may be formed within the body 816.

The spacer 814 includes a spacer body 830 having a coupling portion 832 configured to engage and couple the distal portion 818 of the body 816. The spacer body 830 further defines an orifice 834 which is in communication with the coupling portion 832. In the illustrated embodiment, the spacer body 830 includes thread members 836 and attachment devices 838 formed or otherwise disposed thereon to enable the spacer body 830 to couple to the body 816. Any number or type of thread members 836 and attachment devices 838 may be used to couple the spacer body 830 to the imaging device 812. The distal portion of the spacer body 830 includes a flange 840 defining the orifice 834. In the illustrated embodiment, the flange 840 includes one or more vacuum ports 842 portioned thereon, thereby permitting the flange 840 to engage or couple to the a work surface.

In the illustrated embodiment, the spacer 814 includes one or more vacuum ports 842 which enable the spacer 184 to engage the work surface. Optionally, the spacer body 814 may be configured to avoid contacting the work surface. For example, the spacer body 814 may include an optical system comprised of one or more lenses to enable the imaging device 812 to project and receive light to and from a work surface from a distance without contacting the work surface. For example the optical system may include a zoom lens system.

Further, the spacer 814 may be formed in any variety of shapes and size. For example, the spacer may include a doughnut-shaped spaces. Furthermore, the spacer 814 may include a bladder or cushion filled with any variety of fluids. Optionally, the fluid may be optically transparent.

Figure 27:
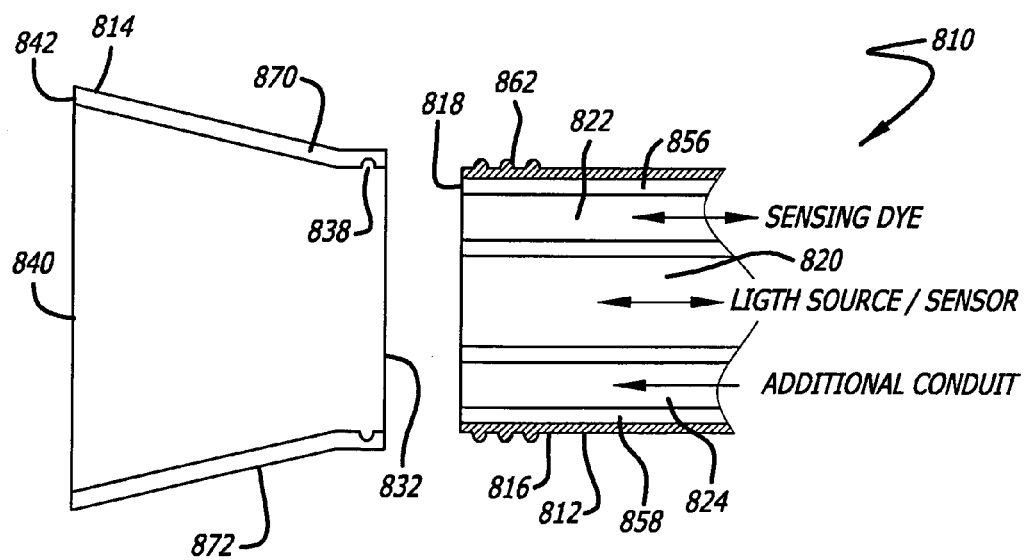
FIG. 27 shows a side cross sectional view of the imaging system shown in FIG. 26.

FIG. 27 shows a cross sectional view of an embodiment of a reflectance avoidance imaging system 810. As shown, the body 816 includes the imaging conduit 820, the secondary imaging conduit 822, and the addition conduit 824 formed therein. In addition, vacuum conduits 856 and 858 are formed within the body 816 and a couple to a vacuum source. (not shown) The spacer 814 includes vacuum conduits 870 and 872 which are in communication with the vacuum conduits 856 and 858 of the body 816 and the vacuum ports 842 formed on the spacer 814. Optionally, one or more attachment members 862 may be positioned on the body 816 to further enable coupling of the spacer 814 to the body 816.

In addition to the novel imaging devices described above, the present application describes a method of imaging and determining various biological parameters non-invasively and, if needed, treating an affected area. For example, when operating the above-described system in an OPS imaging mode, flow though the capillaries and related circulatory structures may be examined be viewing red blood flow therethrough. To operate the system in an OPS imaging mode, the user irradiates the examination substrate with white light. The white light is polarized by a polarizer prior to illuminating the examination substrate. Reflected light is captured by the light guide and transmitted to the polarizing section 42 of the OPS imaging module 30 (See FIG. 2). Light reflected by the system optics and the patient's tissue surface undergoes a polarization shift as a function of scattering and, thus, is cancelled by the polarizing section 42. As such, sub-surface reflected light fails to undergo a polarization shift and will be captured by the image capture device 50, thereby enabling sub-surface imaging. Optionally, OPS imaging may be accomplished in combination with dark field illumination.

Similarly, the imaging system described herein may be used to perform reflectance spectrophotometry using the reflectance spectrophotometry module. A spectrophotometer may be used with the present imaging system to examine the spectral reflectance of the tissue surface. Light from a light source illuminates an examination substrate. The light may comprise an internal light source 18, external light source 20, and/or an ancillary light source 22. (See FIG. 1). Light reflected by the examination substrate 16 is captured by a light transport section 14 and transmitted to a reflectance spectrophotometry module. The spectral characteristic of the reflected light may then be examined and used to determine the hemoglobin saturation, and/or hematocrit concentration within the surface of an organ under investigation.

Lastly, the imaging system described herein may be used to determine the oxygenation and/or functional state of a tissue cell using the fluorescence imaging module. For example, an examination area may be illuminated with UV light thereby targeting the mitochondrial energy state therein. For example, light having a wavelength of about 360 nm may be used to illuminate the examination substrate. Thereafter, light reflected by the substrate may be captured by the light transport section 14 and transmitted to the analyzing section 12. (See FIG. 1) The captured light may undergo a lambda shift from 360 nm to about 460 nm. Thereafter, a fluorescence imaging module 34 may analyze the reflected light for to determine the presence of NADH in the cells, thereby showing availability of oxygen within the cells.

The OPS imaging processor 52, RFS processor 72, and fluorescence imaging processor 92 may each contain any number of formulas, algorithms, models, databases, look-up tables, or related information to compute and display their respective reflectance measurements. For example, Beers-Lambert law may be used to determine the concentration of material in the examination substrate based on the absorbance of the light by the examination substrate.

Also disclosed herein is a method of comprehensively monitoring the microcirculation of a patient. The method may include using any of the aforementioned imaging systems disclosed herein. In one embodiment, the method includes illuminating a tissue substrate, avoiding the reflection of light from the surface of the tissue substrate, receiving light from the tissue substrate, utilizing some of the received light to image microcirculatory flow in the tissue substrate, utilizing some of the received light to determine oxygen availability in the microcirculation, and utilizing some of the received light to determine the adequacy of oxygenation of the tissue cells.

In one embodiment, the aforementioned method may include utilizing the microcirculatory flow information, the oxygen availability information, and the adequacy of oxygenation of tissue cells information, making an early and sensitive determination regarding states of shock, such as septic, hypovolemic, cardiogenic and obstructive septic shock, in patients, and guiding resuscitation therapies aimed at correcting this condition.

In another embodiment the aforementioned method may also include utilizing the microcirculatory flow information, the oxygen availability information, and the adequacy of oxygenation of tissue cells information, and making an early and sensitive determination regarding cardiovascular disease and failure of the patient.

In closing, it is understood that the embodiments of the invention disclosed herein are illustrative of the principals of the invention. Other modifications may be employed which are within the scope of the present invention. Accordingly, the present invention is not limited to that precisely as shown and described in the present disclosure.

What is claimed is:

1. A handheld system for sidestream dark field imaging of tissue beneath a tissue surface, comprising:
   an elongate body portion including an imaging passage extending along a length of the elongate body portion;
   one or more illumination passages which are disposed radially about the imaging passage within the elongate body portion and which are optically isolated from the imaging passage along an entire length of the imaging passage for surface reflection avoidance or reduction when an examination tip of the elongate body portion is proximate the tissue surface;
   a plurality of light emitting diodes which are disposed within the one or more illumination passages, which are disposed in a distal portion of the elongate body portion, which are disposed in a position configured to be in close proximity to the tissue surface during use, and which are configured to directly project light onto a first tissue site via the one or more illumination passages; and
   an image capture device comprising a camera optically coupled to the imaging passage and configured to capture image data of tissue beneath the tissue surface from a second tissue site different from and adjacent to the first tissue site.

2. The system of claim 1 further comprising at least one isolation surface which is configured to optically isolate an illumination field of the first tissue site from an imaging field of the second tissue site.

3. The system of claim 1 further comprising a disposable detachable cap disposed over a distal portion of the elongate body portion having a distal window configured to allow illumination and imaging therethrough.

4. The system of claim 1 further comprising an annular spacer disposed on the distal end of the elongate body portion configured to minimize mechanical contact by the distal portion of the body portion with the second tissue site.

5. The system of claim 1 wherein the light emitting diodes comprise green light emitting diodes.

6. The system of claim 1 further comprising a handle secured to the elongate body portion and configured to be held by a user.

7. A method of imaging tissue beneath a tissue surface, comprising:
provide a system for side stream dark field imaging of tissue beneath a tissue surface, including:
an elongate body portion including an imaging passage extending along a length of the elongate body portion,
one or more illumination passages which are disposed radially about the imaging passage within the elongate body portion and which are optically isolated from the imaging passage along an entire length of the imaging passage for surface reflection avoidance or reduction when an examination tip of the elongate body portion is proximate the tissue surface,
one or more emitters which are disposed within the one or more illumination passages, which are disposed in a distal portion of the elongate body portion, which are disposed in a position configured to be in close proximity to the tissue surface during use, and which are configured to directly project light onto a first tissue site via the one or more illumination passages, and
an image capture device comprising a camera optically coupled to the imaging passage;
emitting light from the one or more emitters onto the first tissue site;
gathering light from a second tissue site through the imaging passage with the image capture device and imaging tissue beneath a surface of the second tissue site.

8. The method of claim 7 wherein the imaged tissue of the second tissue site comprises sublingual tissue.

9. The method of claim 7 wherein the imaged tissue of the second tissue site comprises microcapillaries.

* * * * *

UNITED STATES PATENT AND TRADEMARK OFFICE
CERTIFICATE OF CORRECTION

PATENT NO. : 8,064,976 B2
APPLICATION NO. : 10/956610
DATED : November 22, 2011
INVENTOR(S) : Can Ince It is certified that error appears in the above-identified patent and that said Letters Patent is hereby corrected as shown below:

On the Title page, item (54) and in the Specification, column 1, lines 1-2, please correct the title to read: SYSTEMS AND METHODS FOR SIDESTREAM DARK FIELD IMAGING.

Signed and Sealed this
Twenty-seventh Day of August, 2013

Teresa Stanek Rea
*Acting Director of the United States Patent and Trademark Office*